US010752656B2

(12) United States Patent
Stupp et al.

(10) Patent No.: US 10,752,656 B2
(45) Date of Patent: Aug. 25, 2020

(54) ANTI-MICROBIAL SUPRAMOLECULAR STRUCTURES

(71) Applicants: Northwestern University, Evanston, IL (US); Nanyang Technological University, Singapore (SG)

(72) Inventors: Samuel I. Stupp, Evanston, IL (US); Zhilin Yu, Evanston, IL (US); Nam-Joon Cho, Singapore (SG); Joshua A. Jackman, Singapore (SG)

(73) Assignees: Northwestern University, Evanston, IL (US); Nanyang Technological Unversity, Singapore (SG)

( * ) Notice: Subject to any disclaimer, the term of this patent is extended or adjusted under 35 U.S.C. 154(b) by 0 days.

(21) Appl. No.: 15/789,279

(22) Filed: Oct. 20, 2017

(65) Prior Publication Data

US 2018/0111963 A1 Apr. 26, 2018

Related U.S. Application Data

(60) Provisional application No. 62/410,902, filed on Oct. 21, 2016.

(51) Int. Cl.
| | |
|---|---|
| *A61K 9/00* | (2006.01) |
| *A61K 38/00* | (2006.01) |
| *A61K 38/02* | (2006.01) |
| *C07K 2/00* | (2006.01) |
| *C07K 5/00* | (2006.01) |
| *C07K 7/06* | (2006.01) |
| *A61K 45/06* | (2006.01) |
| *A61K 47/54* | (2017.01) |
| *A01N 25/10* | (2006.01) |
| *A61K 38/08* | (2019.01) |

(52) U.S. Cl.
CPC ............... *C07K 7/06* (2013.01); *A01N 25/10* (2013.01); *A61K 38/08* (2013.01); *A61K 45/06* (2013.01); *A61K 47/542* (2017.08); *A61K 38/00* (2013.01)

(58) Field of Classification Search
None
See application file for complete search history.

(56) References Cited

U.S. PATENT DOCUMENTS

| | | | |
|---|---|---|---|
| 7,030,167 B2 | 4/2006 | Gunther | |
| 7,371,719 B2 | 5/2008 | Stupp et al. | |
| 7,452,679 B2 | 11/2008 | Stupp | |
| 7,491,690 B2 | 2/2009 | Stupp et al. | |
| 7,534,761 B1 | 5/2009 | Stupp et al. | |
| 7,544,661 B2 | 6/2009 | Stupp et al. | |
| 7,554,021 B2 | 6/2009 | Stupp et al. | |
| 7,683,025 B2 | 3/2010 | Stupp et al. | |
| 7,745,708 B2 | 6/2010 | Stupp et al. | |
| 7,838,491 B2 | 11/2010 | Stupp et al. | |
| 7,851,445 B2 | 12/2010 | Stupp et al. | |
| 8,063,014 B2 | 11/2011 | Stupp et al. | |
| 8,076,295 B2 | 12/2011 | Hulvat | |
| 8,080,262 B2 | 12/2011 | Lee et al. | |
| 8,114,834 B2 | 2/2012 | Hsu | |
| 8,114,835 B2 | 2/2012 | Mata | |
| 8,124,583 B2 | 2/2012 | Stupp et al. | |
| 8,138,140 B2 | 3/2012 | Stupp et al. | |
| 8,236,800 B2 | 8/2012 | Degrado et al. | |
| 8,450,271 B2 | 5/2013 | Shah et al. | |
| 8,512,693 B2 | 8/2013 | Capito et al. | |
| 8,546,338 B2 | 10/2013 | Donners | |
| 8,580,923 B2 | 11/2013 | Stupp et al. | |
| 8,748,569 B2 | 6/2014 | Stupp et al. | |
| 8,772,228 B2 | 7/2014 | Stupp et al. | |
| 9,011,914 B2 | 4/2015 | Foo | |
| 9,040,626 B2 | 5/2015 | Chien | |
| 9,044,514 B2 | 6/2015 | Xu et al. | |
| 2012/0294902 A1 | 11/2012 | Stupp et al. | |
| 2014/0027655 A1 | 1/2014 | Reches | |

FOREIGN PATENT DOCUMENTS

| | | |
|---|---|---|
| WO | WO 2016149363 A1 | 9/2016 |
| WO | WO 2016168302 A1 | 10/2016 |

OTHER PUBLICATIONS

Salwiczek et al., "Fluorinated amino acids: compatibility with native protein structures and effects on protein-protein interactions," Chem. Soc. Rev. 41:2135-2171 (2012) (Year: 2012).*
Anraku et al., Systemically Injectable Enzyme-Loaded Polyion Complex Vesicles as In Vivo Nanoreactors Functioning in Tumors, Angew Chem Int Ed, vol. 55(2), pp. 560-565, 2015.
Berendsen et al., Interaction Models for Water in Relation to Protein Hydration. In Intermolecular Forces: Proceedings of the Fourteenth Jerusalem Symposium on Quantum Chemistry and Biochemistry Held in Jerusalem, Israel, Apr. 13-16, 1981; Pullman, B., Ed.; Springer Netherlands: Dordrecht, 1981; pp. 331-342.
Cook et al., Recent Developments in the Preparation and Chemistry of Metallacycles and Metallacages via Coordination, Chem Rev, vol. 115(15), pp. 7001-7045, 2015.
Cotelle et al., Anion-π Enzymes, ACS Cent Sci, vol. 2(6), pp. 388-393, 2016.
Cui et al., Amino Acid Sequence in Constitutionally Isomeric Tetrapeptide Amphiphiles Dictates Architecture of One-Dimensional Nanostructures, J Am Chem Soc, vol. 136(35), pp. 12461-12468, 2014.
Cui et al., Self-Assembly of Peptide Amphiphiles: From Molecules to Nanostructures to Biomaterials, Biopolymers, vol. 94(1), pp. 1-18, 2010.

(Continued)

*Primary Examiner* — Julie Ha
*Assistant Examiner* — Kristina M Hellman
(74) *Attorney, Agent, or Firm* — Casimir Jones, S.C.; David W. Staple

(57) ABSTRACT

Supramolecular structures comprising noncovalently associated peptide amphiphiles and lipids are provided. In particular, provided herein are supramolecular nanostructures of peptide amphiphiles and lipids, co-assembly of which is driven by anion-π interactions, and methods of preparation and use (e.g., as an antimicrobial agent) thereof.

10 Claims, 21 Drawing Sheets
(20 of 21 Drawing Sheet(s) Filed in Color)
Specification includes a Sequence Listing.

(56) References Cited

OTHER PUBLICATIONS

Dankers et al., A modular and supramolecular approach to bioactive scaffolds for tissue engineering, Nat Mater, vol. 4(7), pp. 568-574, 2005.
Davis et al., Evidence of RNAi in humans from systemically administered siRNA via targeted nanoparticles, Nature, vol. 464(7291), pp. 1067-1070, 2010.
Dawson et al., Experimental evidence for the functional relevance of anion-pi interactions, Nat Chem, vol. 2(7), pp. 533-538, 2010.
Discher et al., Polymer vesicles, Science, vol. 297(5583), pp. 967-973, 2002.
Douliez et al., Self-assembly of fatty acids: from foams to protocell vesicles, New J Chem, vol. 38, pp. 5142-5148, 2014.
Fameau et al., Self-assembly of fatty acids in the presence of amines and cationic components, Adv Colloid Interface Sci, vol. 207, pp. 43-64, 2014.
Frontera et al., Putting anion-$\pi$ interactions into perspective, Angew Chem Int Ed Engl, vol. 50(41), pp. 9564-9583, 2011.
Giese et al., Experimental investigation of anion-$\pi$ interactions—applications and biochemical relevance, Chem Commun (Camb), vol. 52(9), pp. 1778-1795, 2016.
Giese et al., Single-Crystal X-ray Diffraction and Solution Studies of Anion-$\pi$ Interactions in N-(Pentafluorobenzyl)pyridinium Salts, Eur J Org Chem, vol. 2014(12), pp. 2435-2442, 2014.
Gu et al., Precise engineering of targeted nanoparticles by using self-assembled biointegrated block copolymers, PNAS, vol. 105(7), pp. 2586-2591, 2008.
Gursky et al., Temperature-dependent $\beta$-sheet formation in $\beta$-amyloid A$\beta$1-40 peptide in water: uncoupling $\beta$-structure folding from aggregation, Biochim Biophys Acta, vol. 1476(1), pp. 93-102, 2000.
Hartgerink et al., Self-Assembly and Mineralization of Peptide-Amphiphile Nanofibers, Science, vol. 294(5547), pp. 1684-1688, 2001.
Hobza et al., Introduction: Noncovalent Interactions, Chem Rev, vol. 116(9), pp. 4911-4912, 2016.
Hong et al., Clustering of Fluorine-Substituted Alcohols as a Factor Responsible for Their Marked Effects on Proteins and Peptides, J Am Chem Soc, vol. 121(37), pp. 8427-8433, 1999.
Huang et al., Programmable Assembly of Nanoarchitectures Using Genetically Engineered Viruses, Nano Lett, vol. 5(7), pp. 1429-1434, 2005.
Israelachvili, J. N., Intermolecular and surface forces; 2nd ed.; Academic: London San Diego, 1992.
Jackman et al., Nanotechnology Formulations for Antibacterial Free Fatty Acids and Monoglycerides, Molecules, vol. 21(3), 305, 2016.
Jain et al., Lone pair ••• $\pi$ interactions between water oxygens and aromatic residues: Quantum chemical studies based on high-resolution protein structures and model compounds, Protein Sci, vol. 18(3), pp. 595-605, 2009.
Lee et al., Atomistic Molecular Dynamics Simulations of Peptide Amphiphile Self-Assembly into Cylindrical Nanofibers, J Am Chem Soc, vol. 133(10), pp. 3677-3683, 2011.
Liu et al., Self-assembled cationic peptide nanoparticles as an efficient antimicrobial agent, Nat Nanotechnol, vol. 4, pp. 457-463, 2009.
Lucas et al., A thorough anion-$\pi$ interaction study in biomolecules: on the importance of cooperativity effects, Chem Sci, vol. 7, pp. 1038-1050, 2016.
Ma et al., The Cation-$\pi$ Interaction, Chem Rev, vol. 97(5), pp. 1303-1324, 1997.

Mayo et al., A recipe for designing water-soluble, $\beta$-sheet-forming peptides, Protein Science, vol. 5(7), pp. 1301-1315, 1996.
Meng et al., Antimicrobial Activity and Protease Stability of Peptides Containing Fluorinated Amino Acids, J Am Chem Soc, vol. 129(50), pp. 15615-15622, 2007.
Meyer et al., Interactions with aromatic rings in chemical and biological recognition, Angew Chem Int Ed Engl, vol. 42(11), pp. 1210-1250, 2003.
Mitra et al., Antimicrobial activity, biocompatibility and hydrogelation ability of dipeptide-based amphiphiles, Org Biomol Chem, vol. 7(1), pp. 94-102, 2009.
Moyer et al., Tuning Nanostructure Dimensions with Supramolecular Twisting, J Phys Chem B, vol. 117(16), pp. 4604-4610, 2013.
Ong et al., Effect of stereochemistry, chain length and sequence pattern on antimicrobial properties of short synthetic $\beta$-sheet forming peptide amphiphiles, Biomaterials, vol. 35(4), pp. 1315-1325, 2014.
Pace et al., Exploring and exploiting polar-$\pi$ interactions with fluorinated aromatic amino acids, Acc Chem Res, vol. 46(4), pp. 907-915, 2013.
Pashuck et al., Direct Observation of Morphological Tranformation from Twisted Ribbons into Helical Ribbons, J Am Chem Soc, vol. 132(26), pp. 8819-8821, 2010.
Pashuck et al., Tuning Supramolecular Rigidity of Peptide Fibers through Molecular Structure, J Am Chem Soc, vol. 132(17), pp. 6041-6046, 2010.
Percec et al., Self-assembly of Janus dendrimers into uniform dendrimersomes and other complex architectures, Science, vol. 328(5981), pp. 1009-1014, 2010.
Perraud et al., Combined cation-$\pi$ and anion-$\pi$ interactions for zwitterion recognition, Angew Chem Int Ed Engl, vol. 51(2), pp. 504-508, 2012.
Quinonero et al., Anion-pi Interactions: do they exist?, Angew Chem Int ed Engl, vol. 41(18), pp. 3389-3392, 2002.
Rekharsky et al., A synthetic host-guest system achieves avidin-biotin affinity by overcoming enthalpy—entropy compensation, PNAS, vol. 204(52), pp. 20737-20742, 2007.
Ringler et al., Self-assembly of proteins into designed networks, Science, vol. 302(5642), pp. 106-109, 2003.
Schottel et al., Anion-pi interactions, Chem Soc Rev, vol. 37(1), pp. 68-83, 2008.
Scott et al., The GROMOS Biomolecular Simulation Program Package, J Phys Chem A, vol. 103(19), pp. 3596-3607, 1999.
Silva et al., Selective Differentiation of Neural Progenitor Cells by High-Epitope Density Nanofibers, Science, vol. 303(5662), pp. 1352-1355, 2004.
Soukasene et al., Anti-Tumor Activity of Peptide Amphiphile Nanofiber-Encapsulated Camptothecin, vol. 5(11), pp. 9113-9121, 2011.
Srinivas et al., Peptidomimetic antibiotics target outer-membrane biogenesis in Pseudomonas aeruginosa, Science, vol. 327(5968), pp. 1010-1013, 2010.
Tsamaloukas et al., Uptake and release protocol for assessing membrane binding and permeation by way of isothermal titration calorimetry, Nat Protocols, vol. 2, pp. 695-704, 2007.
Webber et al., Supramolecular biomaterials, Nat Mater, vol. 15(1), pp. 13-26, 2016.
Wurthner et al., Perylene Bisimide Dye Assemblies as Archetype Functional Supramolecular Materials, Chem Rev, vol. 116(3), pp. 962-1052, 2016.
Zhao et al., Unorthodox Interactions at Work, J Am Chem Soc, vol. 138(13), pp. 4270-4277, 2016.
International Search Report of related PCT/US2017/57580, dated Jan. 17, 2018, 9 pages.

* cited by examiner

FIG. 3C
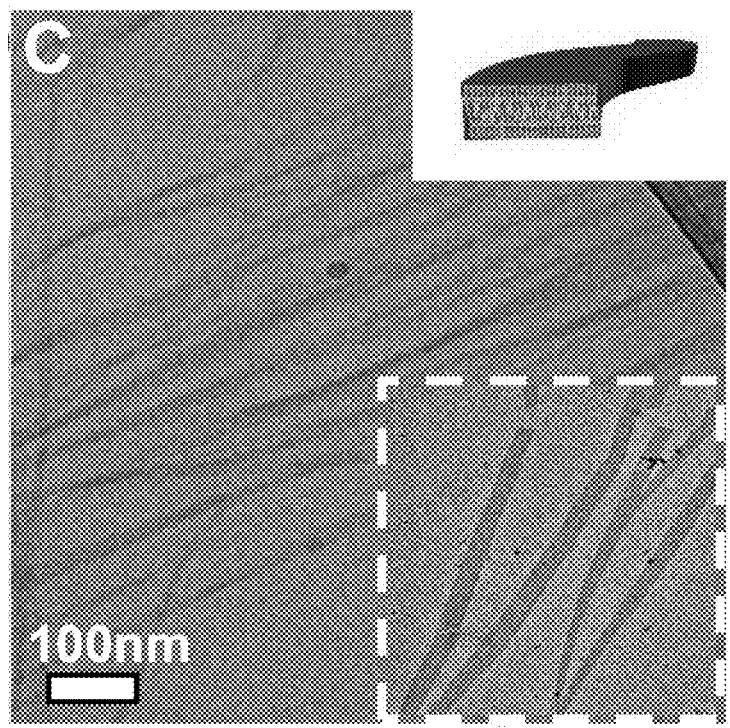
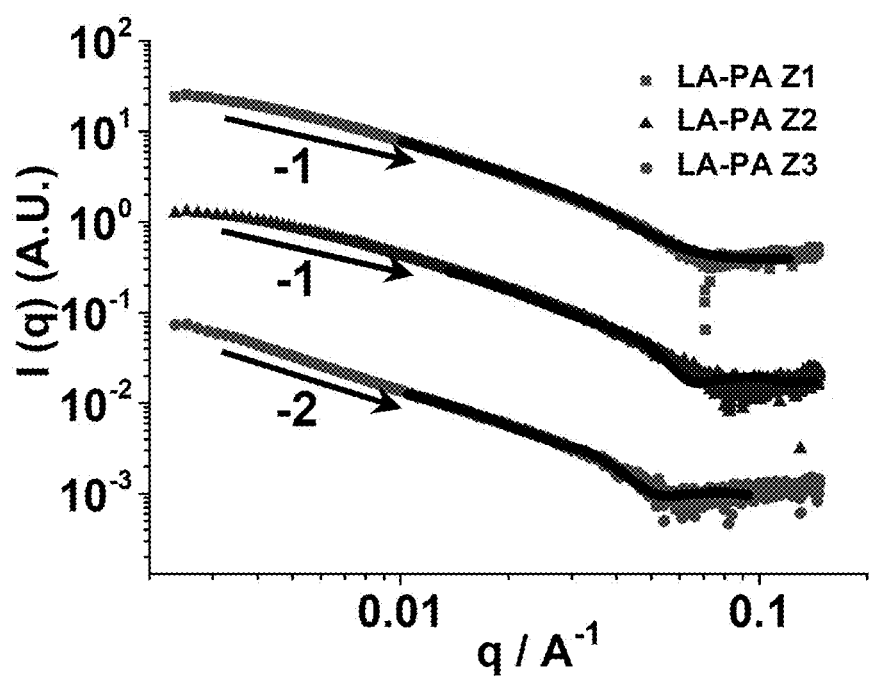
FIG. 3D

FIG. 3E
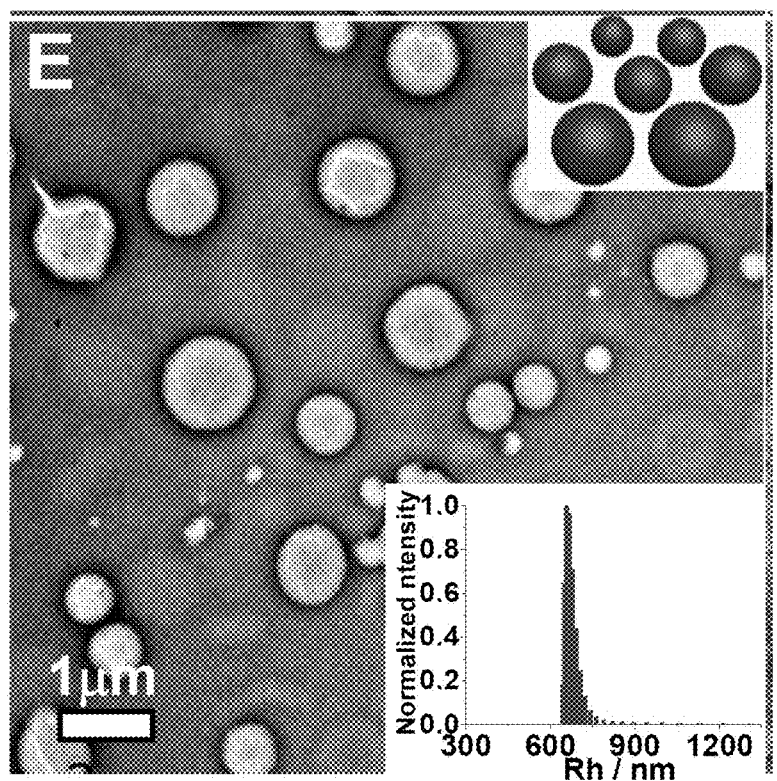
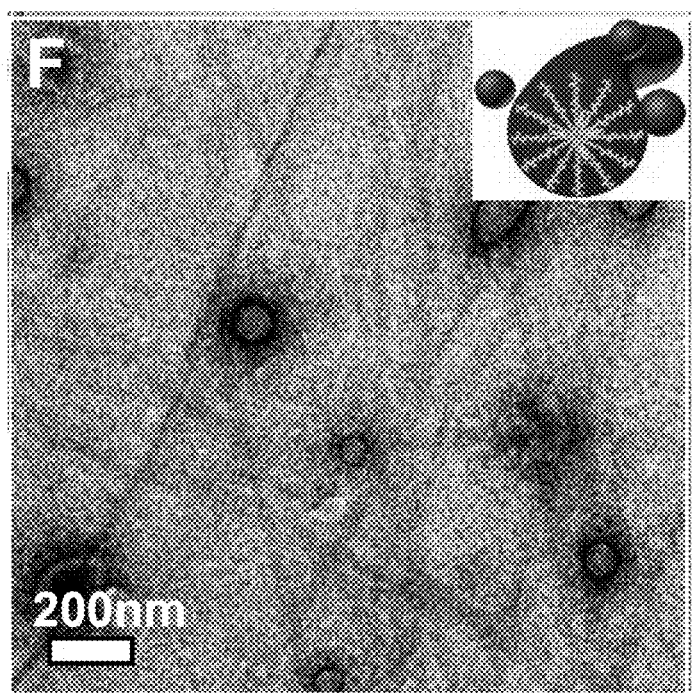
FIG. 3F

FIG. 3G
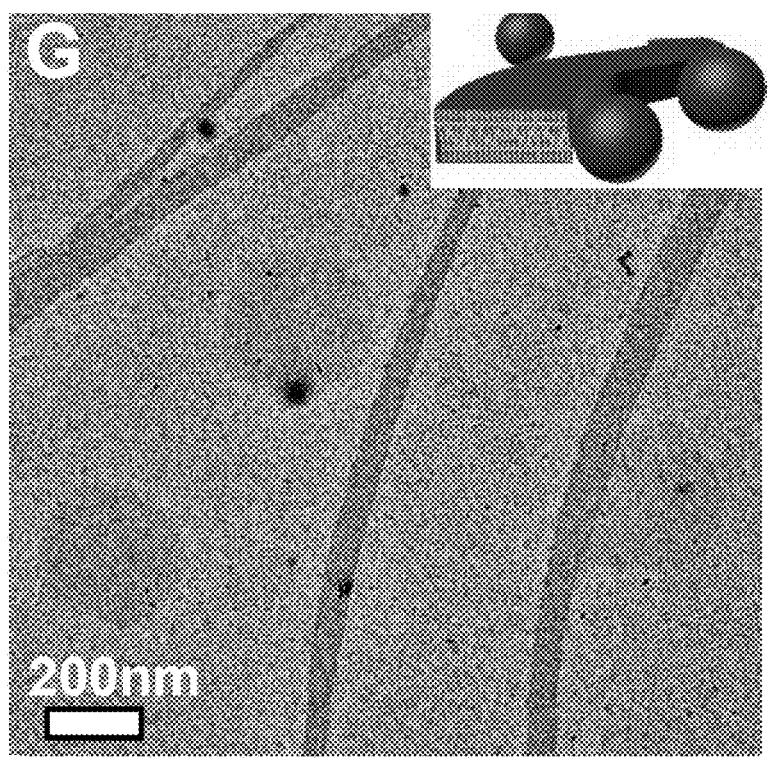
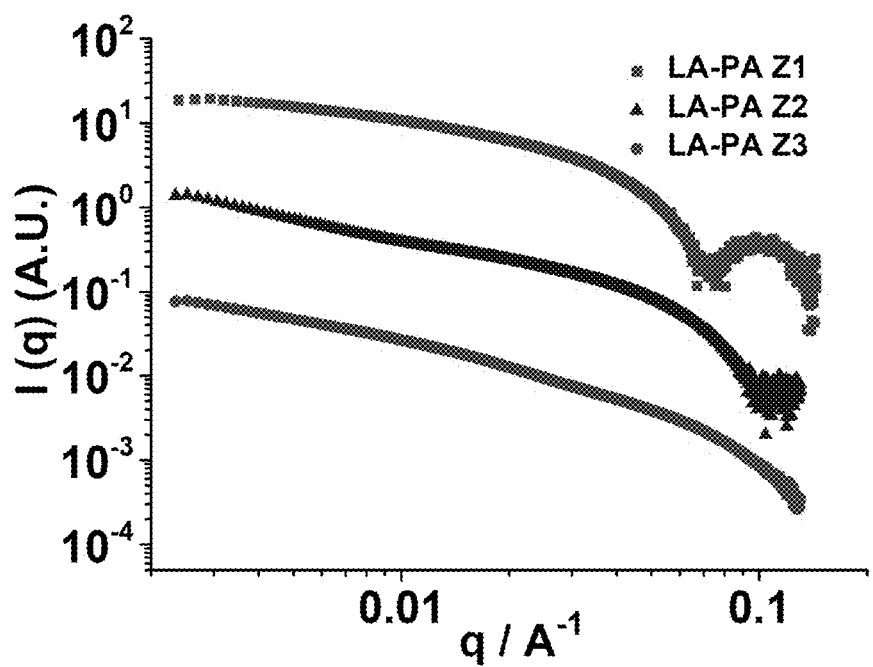
FIG. 3H

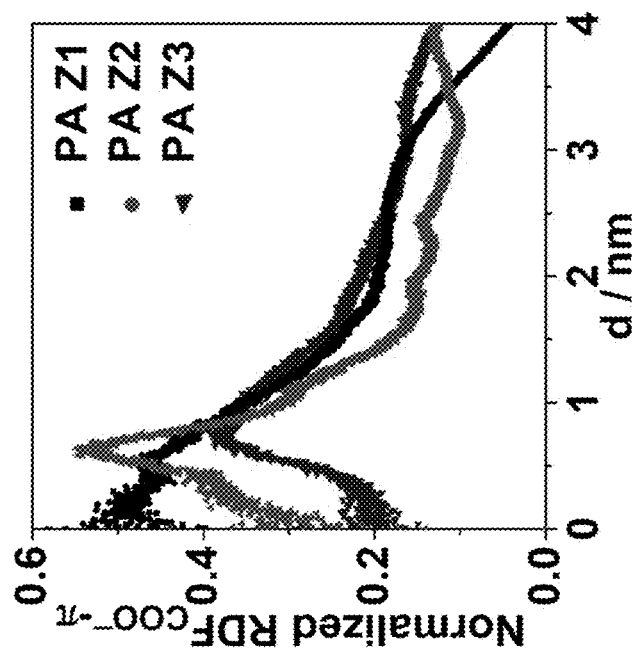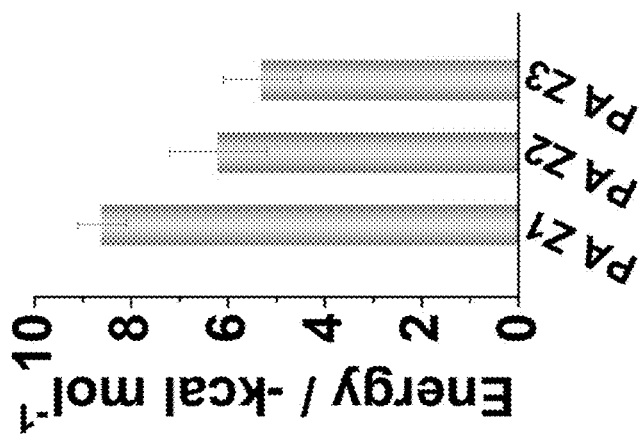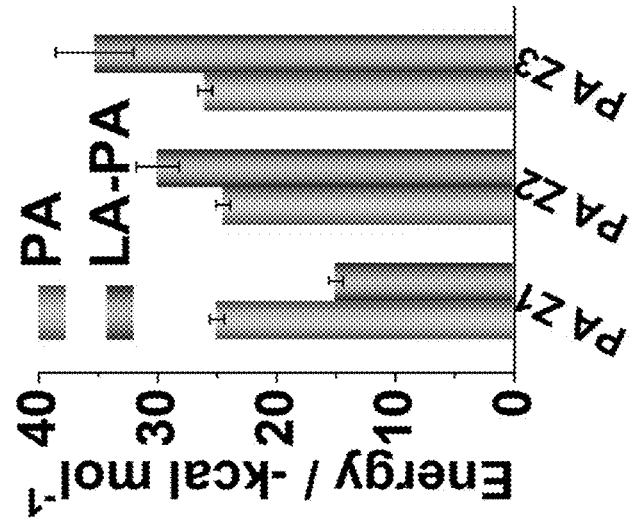
FIG. 5A
FIG. 5B
FIG. 5C

| Composition | Parent PA | PA Z1 | PA Z2 | PA Z3 |
|---|---|---|---|---|
| 1:0 PA:LA | 500 μM* | >500 μM | >500 μM | >500 μM |
| 1:0.4 PA:LA | >500 μM | >500 μM | >500 μM | >500 μM |
| 1:1 PA:LA | 500 μM* | 500 μM* | 500 μM* | 500 μM* |

MRC-5 human fibroblast cell number was 5 x 103, and CCK-8 assay was performed in order to measure dehydrogenase activity. *indicates no more than 20% drop in cell viability.

Control    + 500 μM PA Z1

FIG. 9

Recorded Minimum Inhibitory Concentrations

| Composition | Parent PA | PA Z1 | PA Z2 | PA Z3 |
|---|---|---|---|---|
| 1:0 PA:LA | >500 μM | 4 μM | 4 μM | >500 μM |
| 1:0.4 PA:LA | >500 μM | 4 μM | 4 μM | >500 μM |
| 1:1 PA:LA | >500 μM | 8 μM | 16 μM | >500 μM |

Bacterial cell density was $5 \times 10^5$ CFU/mL, as determined by optical density measurements on cell suspensions.

SEQUENCE LISTING

<160> NUMBER OF SEQ ID NOS: 33

<210> SEQ ID NO 1
<211> LENGTH: 6
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa = pentafluorophenylalanine

<400> SEQUENCE: 1

Xaa Val Val Ala Ala Ala
1               5

<210> SEQ ID NO 2
<211> LENGTH: 6
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa = pentafluorophenylalanine

<400> SEQUENCE: 2

Val Xaa Val Ala Ala Ala
1               5

<210> SEQ ID NO 3
<211> LENGTH: 6
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: Xaa = pentafluorophenylalanine

<400> SEQUENCE: 3

Val Val Xaa Ala Ala Ala
1               5

<210> SEQ ID NO 4
<211> LENGTH: 6
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Xaa = pentafluorophenylalanine

<400> SEQUENCE: 4

Val Val Val Xaa Ala Ala
1               5

<210> SEQ ID NO 5
<211> LENGTH: 6
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE

```
<222> LOCATION: (5)..(5)
<223> OTHER INFORMATION: Xaa = pentafluorophenylalanine

<400> SEQUENCE: 5

Val Val Val Ala Xaa Ala
1               5

<210> SEQ ID NO 6
<211> LENGTH: 6
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: Xaa = pentafluorophenylalanine

<400> SEQUENCE: 6

Val Val Val Ala Ala Xaa
1               5

<210> SEQ ID NO 7
<211> LENGTH: 6
<212> TYPE: PRT
<213> ORGANISM: Artificial sequence
<220> FEATURE:
<223> OTHER INFORMATION: Synthetic peptide

<400> SEQUENCE: 7

Val Val Val Ala Ala Ala
1               5

<210> SEQ ID NO 8
<211> LENGTH: 4
<212> TYPE: PRT
<213> ORGANISM: Artificial sequence
<220> FEATURE:
<223> OTHER INFORMATION: Synthetic peptide

<400> SEQUENCE: 8

Val Val Ala Ala
1

<210> SEQ ID NO 9
<211> LENGTH: 9
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa = pentafluorophenylalanine

<400> SEQUENCE: 9

Xaa Val Val Ala Ala Ala Glu Glu Glu
1               5

<210> SEQ ID NO 10
<211> LENGTH: 9
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa = pentafluorophenylalanine
```

<400> SEQUENCE: 10

Val Xaa Val Ala Ala Ala Glu Glu Glu
1               5

<210> SEQ ID NO 11
<211> LENGTH: 9
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: Xaa = pentafluorophenylalanine

<400> SEQUENCE: 11

Val Val Xaa Ala Ala Ala Glu Glu Glu
1               5

<210> SEQ ID NO 12
<211> LENGTH: 9
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Xaa = pentafluorophenylalanine

<400> SEQUENCE: 12

Val Val Val Xaa Ala Ala Glu Glu Glu
1               5

<210> SEQ ID NO 13
<211> LENGTH: 9
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: Xaa = pentafluorophenylalanine

<400> SEQUENCE: 13

Val Val Val Ala Xaa Ala Glu Glu Glu
1               5

<210> SEQ ID NO 14
<211> LENGTH: 9
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: Xaa = pentafluorophenylalanine

<400> SEQUENCE: 14

Val Val Val Ala Ala Xaa Glu Glu Glu
1               5

<210> SEQ ID NO 15
<211> LENGTH: 9
<212> TYPE: PRT
<213> ORGANISM: Artificial sequence

```
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: Xaa = pentafluorophenylalanine

<400> SEQUENCE: 15

Val Val Val Ala Ala Ala Xaa Glu Glu
1               5

<210> SEQ ID NO 16
<211> LENGTH: 9
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (8)..(8)
<223> OTHER INFORMATION: Xaa = pentafluorophenylalanine

<400> SEQUENCE: 16

Val Val Val Ala Ala Ala Glu Xaa Glu
1               5

<210> SEQ ID NO 17
<211> LENGTH: 9
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (9)..(9)
<223> OTHER INFORMATION: Xaa = pentafluorophenylalanine

<400> SEQUENCE: 17

Val Val Val Ala Ala Ala Glu Glu Xaa
1               5

<210> SEQ ID NO 18
<211> LENGTH: 4
<212> TYPE: PRT
<213> ORGANISM: Artificial sequence
<220> FEATURE:
<223> OTHER INFORMATION: Synthetic peptide

<400> SEQUENCE: 18

Ala Ala Val Val
1

<210> SEQ ID NO 19
<211> LENGTH: 6
<212> TYPE: PRT
<213> ORGANISM: Artificial sequence
<220> FEATURE:
<223> OTHER INFORMATION: Synthetic peptide

<400> SEQUENCE: 19

Ala Ala Ala Val Val Val
1               5

<210> SEQ ID NO 20
<211> LENGTH: 4
<212> TYPE: PRT
<213> ORGANISM: Artificial sequence
<220> FEATURE:
<223> OTHER INFORMATION: Synthetic peptide
```

```
<220> FEATURE:
<221> NAME/KEY: MISC_FEATURE
<222> LOCATION: (1)..(1)
<223> OTHER INFORMATION: Xaa = pentafluorophenylalanine

<400> SEQUENCE: 20

Xaa Val Ala Ala
1

<210> SEQ ID NO 21
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa = pentafluorophenylalanine

<400> SEQUENCE: 21

Val Xaa Ala Ala
1

<210> SEQ ID NO 22
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: Xaa = pentafluorophenylalanine

<400> SEQUENCE: 22

Val Val Xaa Ala
1

<210> SEQ ID NO 23
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Xaa = pentafluorophenylalanine

<400> SEQUENCE: 23

Val Val Ala Xaa
1

<210> SEQ ID NO 24
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa = pentafluorophenylalanine

<400> SEQUENCE: 24

Xaa Glu Lys Lys
1
```

```
<210> SEQ ID NO 25
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa = pentafluorophenylalanine

<400> SEQUENCE: 25

Glu Xaa Lys Lys
1

<210> SEQ ID NO 26
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: Xaa = pentafluorophenylalanine

<400> SEQUENCE: 26

Glu Glu Xaa Lys
1

<210> SEQ ID NO 27
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Xaa = pentafluorophenylalanine

<400> SEQUENCE: 27

Glu Glu Lys Xaa
1

<210> SEQ ID NO 28
<211> LENGTH: 9
<212> TYPE: PRT
<213> ORGANISM: Artificial sequence
<220> FEATURE:
<223> OTHER INFORMATION: Synthetic peptide

<400> SEQUENCE: 28

Val Val Val Ala Ala Ala Glu Glu Glu
1               5

<210> SEQ ID NO 29
<211> LENGTH: 2
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa = pentafluorophenylalanine

<400> SEQUENCE: 29

Xaa Glu
1
```

```
<210> SEQ ID NO 30
<211> LENGTH: 2
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa = pentafluorophenylalanine

<400> SEQUENCE: 30

Glu Xaa
1

<210> SEQ ID NO 31
<211> LENGTH: 3
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa = pentafluorophenylalanine

<400> SEQUENCE: 31

Xaa Glu Glu
1

<210> SEQ ID NO 32
<211> LENGTH: 3
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa = pentafluorophenylalanine

<400> SEQUENCE: 32

Glu Xaa Glu
1

<210> SEQ ID NO 33
<211> LENGTH: 3
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: Xaa = pentafluorophenylalanine

<400> SEQUENCE: 33

Glu Glu Xaa
1
```

US 10,752,656 B2

ANTI-MICROBIAL SUPRAMOLECULAR STRUCTURES

CROSS-REFERENCE TO RELATED APPLICATIONS

The present invention claims priority to U.S. Provisional Patent Application 62/410,902, filed Oct. 21, 2016, which is incorporated by reference in its entirety.

STATEMENT REGARDING FEDERAL FUNDING

This invention was made with government support under DMR15087312 awarded by the National Science Foundation. The government has certain rights in the invention.

FIELD

Supramolecular structures comprising noncovalently associated peptide amphiphiles and lipids are provided. In particular, provided herein are supramolecular nanostructures of peptide amphiphiles and lipids, co-assembly of which is driven by anion-π interactions, and methods of preparation and use (e.g., as an antimicrobial agent) thereof.

BACKGROUND

Due to increasing antibiotic resistance of bacteria, development of new antibacterial agents is important to sustain public health. As one significant category of antibacterial agents, antimicrobial peptides exhibit great potential in treatment for antibiotic-resistant bacterial infection and hence have attracted broad attention in both industrial and academic community. However, current available antimicrobial peptides suffer from low synthetic yield due to their relatively long amino acid sequences, and poor balance between antibacterial activity and biocompatibility.

SUMMARY

Supramolecular structures comprising noncovalently associated peptide amphiphiles and lipids are provided. In particular, provided herein are supramolecular nanostructures of peptide amphiphiles and lipids, co-assembly of which is driven by anion-π interactions, and methods of preparation and use (e.g., as an antimicrobial agent) thereof.

In some embodiments, provided herein are peptide amphiphiles comprising a non-peptide hydrophobic tail, a structural peptide segment, and a charged peptide segment, wherein one amino acid in the peptide amphiphile is a pentafluorophenylalanine (Z) residue.

In some embodiments, the non-peptide hydrophobic tail comprises an acyl chain of 6 to 24 carbons in length. In some embodiments, the structural peptide segment is capable of forming hydrogen bonds and/or other stabilizing interactions with a structural peptide segment from an adjacent peptide amphiphile. In some embodiments, the hydrogen bonds and/or other stabilizing interactions result in structure formation that is detectable by circular dichroism and/or microscopy. In some embodiments, the structural peptide segment is a β-sheet-forming peptide segment.

In some embodiments, the β-sheet-forming peptide segment comprises 3-9 histidine (H), isoleucine (I), leucine (L), phenylalanine (F), and/or alanine (A) amino acids, and 1 pentafluorophenylalanine amino acids. In some embodiments, the β-sheet-forming peptide segment comprises ZVVAAA (SEQ ID NO: 1), VZVAAA (SEQ ID NO: 2), VVZAAA (SEQ ID NO: 3). VVVZAA (SEQ ID NO: 4), VVVAZA (SEQ ID NO: 5), or VVVAAZ (SEQ IS NO: 6). In some embodiments, the charged peptide segment comprises acidic and/or basic amino acid residues. In some embodiments, the charged peptide segment comprises 2-6 acidic residues selected from glutamate (E) and aspartate (D). In some embodiments, the charged peptide segment comprises $(X^a)_{2-4}$, wherein each $X^a$ is an acidic residue selected from E and D. In some embodiments, the charged peptide segment comprises EEE. In some embodiments, the charged peptide segment comprises 2-6 basic residues selected from histidine (H), arginine (R), and lysine (K). In some embodiments, the charged peptide segment comprises $(X^b)_{2-4}$, wherein each $X^b$ is a basic amino acid residue selected from H, R. and K.

In some embodiments, the charged peptide segment comprises 1-5 acidic residues selected from glutamate (E) and aspartate (D), and one pentafluorophenylalanine (Z). In some embodiments, the charged peptide segment comprises ZE (SEQ ID NO: 29), EZ (SEQ ID NO: 30), ZEE (SEQ ID NO: 31), EZE (SEQ ID NO: 32), or EEZ (SEQ ID NO: 33). In some embodiments, the β-sheet-forming peptide segment comprises 4-10 histidine (H), isoleucine (I), leucine (L), phenylalanine (F), and/or alanine (A) amino acids. In some embodiments, the β-sheet-forming peptide segment comprises VVVAAA (SEQ ID NO: 7) or VVAA (SEQ ID NO: 8).

In some embodiments, the structural peptide segment and the charged peptide segment comprise ZVVAAAEEE (SEQ ID NO: 9), VZVAAAEEE (SEQ ID NO: 10), VVZAAAEEE (SEQ ID NO: 11), VVVZAAEEE (SEQ ID NO: 12), VVVAZAEEE (SEQ ID NO: 13), VVVAAZEEE (SEQ ID NO: 14), VVVAAAZEE (SEQ ID NO: 15), VVVAAAEZE (SEQ ID NO: 16), or VVVAAAEEZ (SEQ ID NO: 17).

In some embodiments, provided herein are nanofibers comprising the (Z-containing) peptide amphiphiles described herein. In some embodiments, provided herein are aqueous solutions comprising (Z-containing) peptide amphiphile nanofibers.

In some embodiments, provided herein are supramolecular structures comprising a peptide amphiphile described herein and a lipid molecule. In some embodiments, the lipid molecule is a fatty acid. In some embodiments, the fatty acid comprises 6-24 carbons. In some embodiments, the fatty acid and the non-peptide hydrophobic tail have equal number of carbons. In some embodiments, interaction between the lipid and the peptide amphiphile is driven by lone pair-π interactions between the fatty acid and the pentafluorophenylalanine and anion-π interactions.

In some embodiments, provided herein are methods of treating a microbial infection comprising administering a supramolecular structure described herein. In some embodiments, the microbial infection is a bacterial infection. In some embodiments, the bacteria are antibiotic resistant. In some embodiments, the supramolecular structure is administered with an antibiotic agent.

In some embodiments, provided herein is the use of a supramolecular structure described herein to treat an infection.

BRIEF DESCRIPTION OF THE DRAWINGS

The patent or application file contains at least one drawing executed in color. Copies of this patent or patent application publication with color drawings will be provided by the Office upon request and payment of the necessary fee.

FIFS. 1A-D.

(FIGS. 2A-B) CD spectra of the mixed aqueous solutions of (FIG. 2A) PA Z1, (FIG. 2B) PA Z2, and (FIG. 2C) PA Z3 with lauric acid (LA) aged for 2 hours at 25° C. (FIGS. 2D-E) The CD intensity changes at 200 nm for (FIG. 2D) PAs Z1 and (FIG. 2E) Z2 or the ratios of CD intensities at 194 and 204 nm for (FIG. 2F) PA Z3 as a function of the molar ratio between lauric acid and the PAs.

FIGS. 3A-H. (FIGS. 3A-C) Cryo-TEM images of mixtures of PA Z1, PA Z2, and PA Z3 with lauric acid in a molar ratio of 1:0.4, and (FIGS. 3E-G) conventional TEM images of mixtures in a 1:1 molar ratio without staining (schematic illustrations of the morphologies are shown in the insets). (FIG. 3D and FIG. 3H) SAXS profiles of the LA-PA aqueous solutions in a molar ratio of 1:0.4 (FIG. 3D) and 1:1 (FIG. 3H) displaying the scattered intensity versus the scattering vector q (log-log plot). Scattering intensities are offset vertically for clarity and the fitting curves for the scattering data are shown in black in (FIG. 3D).

(FIG. 4A) Cross-sectional snapshots taken for the PA cylindrical fibers without and with lauric acid in a molar ratio of 1:0.2 after 300 ns simulation (Cyan: alkyl tails in PAs; Blue: LAs: Yellow: β-sheets stands). (FIG. 4B) Percentage of β-sheets in secondary structures of the PAs and their co-assemblies with lauric acid in 1:0.2 molar ratio. (FIG. 4C) Cross-sectional distribution profile of lauric acid molecules in the nanofibers as a function of normalized radius.

FIGS. 5A-C. Simulation-estimated strength of (FIG. 5A) π,π-stacking interactions between the aromatic groups in the PAs in the absence and presence of lauric acid molecules and (FIG. 5B) the anion-π interactions between the PAs and lauric acid molecules (PA:LA=1:0.2). (FIG. 5C) Normalized radial distribution function (RDF) of the distance between the polar carboxylic acid functional group of lauric acid molecules and the mass center of pentafluorobenzene rings within the formed nanofibers (PA:LA=1:0.2).

FIG. 9. Shows the minimum inhibitory concentration (MIC) of the PAs against Staphylococcus aureus.

DEFINITIONS

Figure 1A:
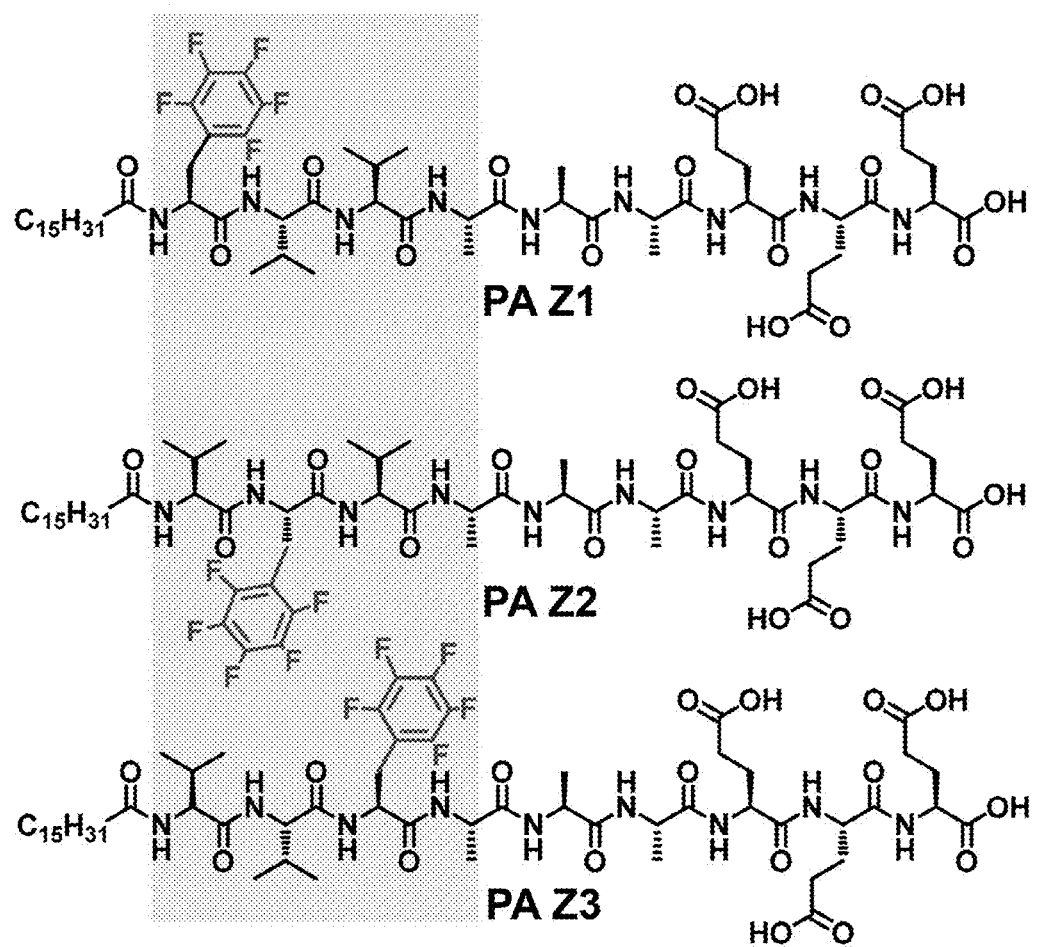
(FIG. 1A) Chemical structures for the designed PA Z1, PA Z2, and PA Z3 containing a pentafluorophenylalanine (Z) at various positions.

Although any methods and materials similar or equivalent to those described herein can be used in the practice or testing of embodiments described herein, some preferred methods, compositions, devices, and materials are described herein. However, before the present materials and methods are described, it is to be understood that this invention is not limited to the particular molecules, compositions, methodologies or protocols herein described, as these may vary in accordance with routine experimentation and optimization. It is also to be understood that the terminology used in the description is for the purpose of describing the particular versions or embodiments only, and is not intended to limit the scope of the embodiments described herein.

Unless otherwise defined, all technical and scientific terms used herein have the same meaning as commonly understood by one of ordinary skill in the art to which this invention belongs. However, in case of conflict, the present specification, including definitions, will control. Accordingly, in the context of the embodiments described herein, the following definitions apply.

As used herein and in the appended claims, the singular forms "a", "an" and "the" include plural reference unless the context clearly dictates otherwise. Thus, for example, reference to "a peptide amphiphile" is a reference to one or more peptide amphiphiles and equivalents thereof known to those skilled in the art, and so forth.

As used herein, the term "comprise" and linguistic variations thereof denote the presence of recited feature(s), element(s), method step(s), etc. without the exclusion of the presence of additional feature(s), element(s), method step(s), etc. Conversely, the term "consisting of" and linguistic variations thereof, denotes the presence of recited feature(s), element(s), method step(s), etc. and excludes any unrecited feature(s), element(s), method step(s), etc., except for ordinarily-associated impurities. The phrase "consisting essentially of" denotes the recited feature(s), element(s), method step(s), etc. and any additional feature(s), element(s), method step(s), etc. that do not materially affect the basic nature of the composition, system, or method. Many embodiments herein are described using open "comprising" language. Such embodiments encompass multiple closed "consisting of" and/or "consisting essentially of" embodiments, which may alternatively be claimed or described using such language.

The term "amino acid" refers to natural amino acids, unnatural amino acids, and amino acid analogs, all in their D and L stereoisomers, unless otherwise indicated, if their structures allow such stereoisomeric forms.

Natural amino acids include alanine (Ala or A), arginine (Arg or R), asparagine (Asn or N), aspartic acid (Asp or D), cysteine (Cys or C), glutamine (Gln or Q), glutamic acid (Glu or E), glycine (Gly or G), histidine (His or H), isoleucine (Ile or I), leucine (Leu or L), Lysine (Lys or K), methionine (Met or M), phenylalanine (Phe or F), proline (Pro or P), serine (Ser or S), threonine (Thr or T), tryptophan (Trp or W), tyrosine (Tyr or Y) and valine (Val or V).

Unnatural amino acids include, but are not limited to, pentafluorophenylalanine ("Z"), azetidinecarboxylic acid, 2-aminoadipic acid, 3-aminoadipic acid, beta-alanine, naphthylalanine ("naph"), aminopropionic acid, 2-aminobutyric acid, 4-aminobutyric acid, 6-aminocaproic acid, 2-aminoheptanoic acid, 2-aminoisobutyric acid, 3-aminoisbutyric acid, 2-aminopimelic acid, tertiary-butylglycine ("tBuG"), 2,4-diaminoisobutyric acid, desmosine, 2,2'-diaminopimelic acid, 2,3-diaminopropionic acid. N-ethylglycine. N-ethylasparagine, homoproline ("hPro" or "homoP"), hydroxylysine, allo-hydroxylysine, 3-hydroxyproline ("3Hyp"), 4-hydroxyproline ("4Hyp"), isodesmosine, allo-isoleucine, N-methylalanine ("MeAla" or "Nime"), N-alkylglycine ("NAG") including N-methylglycine, N-methylisoleucine, N-alkylpentylglycine ("NAPG") including N-methylpentylglycine. N-methylvaline, naphthylalanine, norvaline ("Norval"), norleucine ("Norleu"), octylglycine ("OctG"), omithine ("Orn"), pentylglycine ("pG" or "PGly"), pipecolic acid, thioproline ("ThioP" or "tPro"), homoLysine ("hLys"), and homoArginine ("hArg").

The term "amino acid analog" refers to a natural or unnatural amino acid where one or more of the C-terminal carboxy group, the N-terminal amino group and side-chain bioactive group has been chemically blocked, reversibly or irreversibly, or otherwise modified to another bioactive group. For example, aspartic acid-(beta-methyl ester) is an amino acid analog of aspartic acid; N-ethylglycine is an amino acid analog of glycine: or alanine carboxamide is an amino acid analog of alanine. Other amino acid analogs include methionine sulfoxide, methionine sulfone, S-(carboxymethyl)-cysteine, S-(carboxymethyl)-cysteine sulfoxide and S-(carboxymethyl)-cysteine sulfone.

As used herein, the term "peptide" refers an oligomer to short polymer of amino acids linked together by peptide bonds. In contrast to other amino acid polymers (e.g., proteins, polypeptides, etc.), peptides are of about 50 amino acids or less in length. A peptide may comprise natural amino acids, non-natural amino acids, amino acid analogs, and/or modified amino acids. A peptide may be a subsequence of naturally occurring protein or a non-natural (artificial) sequence.

As used herein, the term "artificial" refers to compositions and systems that are designed or prepared by man, and are not naturally occurring. For example, an artificial peptide, peptoid, or nucleic acid is one comprising a non-natural sequence (e.g., a peptide without 100% identity with a naturally-occurring protein or a fragment thereof).

As used herein, a "conservative" amino acid substitution refers to the substitution of an amino acid in a peptide or polypeptide with another amino acid having similar chemical properties, such as size or charge. For purposes of the present disclosure, each of the following eight groups contains amino acids that are conservative substitutions for one another:

1) Alanine (A) and Glycine (G);
2) Aspartic acid (D) and Glutamic acid (E);
3) Asparagine (N) and Glutamine (Q);
4) Arginine (R) and Lysine (K);
5) Isoleucine (I), Leucine (L), Methionine (M), and Valine (V):
6) Phenylalanine (F), Tyrosine (Y), and Tryptophan (W);
7) Serine (S) and Threonine (T); and
8) Cysteine (C) and Methionine (M).

Naturally occurring residues may be divided into classes based on common side chain properties, for example: polar positive (or basic) (histidine (H), lysine (K), and arginine (R)); polar negative (or acidic) (aspartic acid (D), glutamic acid (E)); polar neutral (serine (S), threonine (T), asparagine (N), glutamine (Q)): non-polar aliphatic (alanine (A), valine (V), leucine (L), isoleucine (I), methionine (M)): non-polar aromatic (phenylalanine (F), tyrosine (Y), tryptophan (W)); proline and glycine; and cysteine. As used herein, a "semi-conservative" amino acid substitution refers to the substitution of an amino acid in a peptide or polypeptide with another amino acid within the same class.

In some embodiments, unless otherwise specified, a conservative or semi-conservative amino acid substitution may also encompass non-naturally occurring amino acid residues that have similar chemical properties to the natural residue. These non-natural residues are typically incorporated by chemical peptide synthesis rather than by synthesis in biological systems. These include, but are not limited to, peptidomimetics and other reversed or inverted forms of amino acid moieties. Embodiments herein may, in some embodiments, be limited to natural amino acids, non-natural amino acids, and/or amino acid analogs.

Non-conservative substitutions may involve the exchange of a member of one class for a member from another class.

As used herein, the term "sequence identity" refers to the degree of which two polymer sequences (e.g., peptide, polypeptide, nucleic acid, etc.) have the same sequential composition of monomer subunits. The term "sequence similarity" refers to the degree with which two polymer sequences (e.g., peptide, polypeptide, nucleic acid, etc.) differ only by conservative and/or semi-conservative amino acid substitutions. The "percent sequence identity" (or "percent sequence similarity") is calculated by: (1) comparing two optimally aligned sequences over a window of comparison (e.g., the length of the longer sequence, the length of the shorter sequence, a specified window, etc.), (2) determining the number of positions containing identical (or similar) monomers (e.g., same amino acids occurs in both sequences, similar amino acid occurs in both sequences) to yield the number of matched positions, (3) dividing the number of matched positions by the total number of positions in the comparison window (e.g., the length of the longer sequence, the length of the shorter sequence, a specified window), and (4) multiplying the result by 100 to yield the percent sequence identity or percent sequence similarity. For example, if peptides A and B are both 20 amino acids in length and have identical amino acids at all but 1 position, then peptide A and peptide B have 95% sequence identity. If the amino acids at the non-identical position shared the same biophysical characteristics (e.g., both were acidic), then peptide A and peptide B would have 100% sequence similarity. As another example, if peptide C is 20 amino acids in length and peptide D is 15 amino acids in length, and 14 out of 15 amino acids in peptide D are identical to those of a portion of peptide C, then peptides C and D have 70% sequence identity, but peptide D has 93.3%6 sequence identity to an optimal comparison window of peptide C. For the purpose of calculating "percent sequence identity" (or "percent sequence similarity") herein, any gaps in aligned sequences are treated as mismatches at that position.

Any polypeptides described herein as having a particular percent sequence identity or similarity (e.g., at least 70%) with a reference sequence ID number, may also be expressed as having a maximum number of substitutions (or terminal deletions) with respect to that reference sequence. For example, a sequence having at least Y % sequence identity (e.g., 90%) with SEQ ID NO:Z (e.g., 100 amino acids) may have up to X substitutions (e.g., 10) relative to SEQ ID NO:Z, and may therefore also be expressed as "having X (e.g., 10) or fewer substitutions relative to SEQ ID NO:Z."

As used herein, the term "nanofiber" refers to an elongated or threadlike filament (e.g., having a significantly greater length dimension that width or diameter) with a diameter typically less than 100 nanometers.

As used herein, the term "supramolecular" (e.g., "supramolecular complex," "supramolecular interactions," "supramolecular fiber," "supramolecular polymer," etc.) refers to the non-covalent interactions between molecules (e.g., polymers, marcomolecules, etc.) and the multicomponent assemblies, complexes, systems, and/or fibers that form as a result.

As used herein, the terms "self-assemble" and "self-assembly" refer to formation of a discrete, non-random, aggregate structure from component parts; said assembly occurring spontaneously through random movements of the components (e.g. molecules) due only to the inherent chemical or structural properties and attractive forces of those components.

As used herein, the term "peptide amphiphile" refers to a molecule that, at a minimum, includes a non-peptide lipophilic (hydrophobic) segment, a structural peptide segment and/or charged peptide segment (often both), and optionally a bioactive segment (e.g., linker segment, bioactive segment, etc.). The peptide amphiphile may express a net charge at physiological pH, either a net positive or negative net charge, or may be zwitterionic (i.e., carrying both positive and negative charges). Certain peptide amphiphiles consist of or comprise: (1) a hydrophobic, non-peptide segment (e.g., comprising an acyl group of six or more carbons), (2) a structural peptide segment (e.g., β-sheet forming); (3) a charged peptide segment, and (4) a bioactive segment (e.g., linker segment).

As used herein, and in the appended claims, the term "lipophilic moiety" or "hydrophobic moiety" refers to the moiety (e.g., an acyl, ether, sulfonamide, or phosphodiestermoiety) disposed on one terminus (e.g., C-terminus, N-terminus) of the peptide amphiphile, and may be herein and elsewhere referred to as the lipophilic or hydrophobic segment or component. The hydrophobic segment should be of a sufficient length to provide amphiphilic behavior and aggregate (or nanosphere or nanofiber) formation in water or another polar solvent system. Accordingly, in the context of the embodiments described herein, the hydrophobic component preferably comprises a single, linear acyl chain of the formula: $C_{n-1}H_{2n-1}C(O)$— where n=2-25. In some embodiments, a linear acyl chain is the lipophilic group (saturated or unsaturated carbons), palmitic acid. However, other lipophilic groups may be used in place of the acyl chain such as steroids, phospholipids and fluorocarbons.

As used herein, the term "structural peptide" refers to a portion of a peptide amphiphile, typically disposed between the hydrophobic segment and the charged peptide segment. The structural peptide is generally composed of three to ten amino acid residues with non-polar, uncharged side chains (e.g., His (H), Val (V), Ile (I), Leu (L), Ala (A), Phe (F)) selected for their propensity to form hydrogen bonds or other stabilizing interactions (e.g., hydrophobic interactions, van der Waals' interactions, etc.) with structural segments of adjacent structural segments. In some embodiments, nanofibers of peptide amphiphiles having structural peptide segments display linear or 2D structure when examined by microscopy and/or α-helix and/or β-sheet character when examined by circular dichroism (CD).

As used herein, the term "beta (β)-sheet-forming peptide segment" refers to a structural peptide segment that has a propensity to display β-sheet-like character (e.g., when analyzed by CD). In some embodiments, amino acids in a beta (1)-sheet-forming peptide segment are selected for their propensity to form a beta-sheet secondary structure. Examples of suitable amino acid residues selected from the twenty naturally occurring amino acids include Met (M), Val (V), lie (I), Cys (C), Tyr (Y), Phe (F), Gin (Q), Leu (L), Thr (T), Ala (A), and Gly (G) (listed in order of their propensity to form beta sheets). However, non-naturally occurring amino acids of similar beta-sheet forming propensity may also be used.

Peptide segments capable of interacting to form beta sheets and/or with a propensity to form beta sheets are understood (See, e.g., Mayo et al. Protein Science (1996), 5:1301-1315; herein incorporated by reference in its entirety).

As used herein, the term "charged peptide segment" refers to a portion of a peptide amphiphile that is rich (e.g., >50%, >75%, etc.) in charged amino acid residues, or amino acid residue that have a net positive or negative charge under physiologic conditions. A charged peptide segment may be acidic (e.g., negatively charged), basic (e.g., positively charged), or zwitterionic (e.g., having both acidic and basic residues).

As used herein, the terms "carboxy-rich peptide segment," "acidic peptide segment," and "negatively-charged peptide segment" refer to a peptide sequence of a peptide amphiphile that comprises one or more amino acid residues that have side chains displaying carboxylic acid side chains (e.g., Glu (E), Asp (D), or non-natural amino acids). A carboxy-rich peptide segment may optionally contain one or more additional (e.g., non-acidic) amino acid residues. Non-natural amino acid residues, or peptidomimetics with acidic side chains could be used, as will be evident to one ordinarily skilled in the art. There may be from about 2 to about 7 amino acids, and or about 3 or 4 amino acids in this segment.

As used herein, the terms "amino-rich peptide segment", "basic peptide segment," and "positively-charged peptide segment" refer to a peptide sequence of a peptide amphiphile that comprises one or more amino acid residues that have side chains displaying positively-charged acid side chains (e.g., Arg (R), Lys (K), His (H), or non-natural amino acids, or peptidomimetics). A basic peptide segment may optionally contain one or more additional (e.g., non-basic) amino acid residues. Non-natural amino acid residues with basic side chains could be used, as will be evident to one ordinarily skilled in the art. There may be from about 2 to about 7 amino acids, and or about 3 or 4 amino acids in this segment.

As used herein, the term "bioactive peptide" refers to amino acid sequences that mediate the action of sequences, molecules, or supramolecular complexes associated there-with. Peptide amphiphiles and structures (e.g., nanofibers) bearing bioactive peptides (e.g., a TF-targeting sequence, etc.) exhibits the functionality of the bioactive peptide. As used herein, the term "biocompatible" refers to materials and agents that are not toxic to cells or organisms. In some embodiments, a substance is considered to be "biocompatible" if its addition to cells in vitro results in less than or equal to approximately 10% cell death, usually less than 5%, more usually less than 1%.

As used herein, "biodegradable" as used to describe the polymers, hydrogels, and/or wound dressings herein refers to compositions degraded or otherwise "broken down" under exposure to physiological conditions. In some embodiments, a biodegradable substance is a broken down by cellular machinery, enzymatic degradation, chemical processes, hydrolysis, etc. In some embodiments, a wound dressing or coating comprises hydrolyzable ester linkages that provide the biodegradability.

As used herein, the phrase "physiological conditions" relates to the range of chemical (e.g., pH, ionic strength) and biochemical (e.g., enzyme concentrations) conditions likely to be encountered in the intracellular and extracellular fluids of tissues. For most tissues, the physiological pH ranges from about 7.0 to 7.4.

As used herein, the term "microbe" refers to cellular microorganisms including bacteria, fungi, and archaea, and encompasses both individual organisms and populations comprising any number of the organisms.

The terms "pathogen" and "pathogenic" in reference to a microorganism (e.g., bacteria) includes any such microorganism that is capable of causing or affecting a disease, disorder or condition of a host containing the microorganism.

As used herein, the term "antimicrobial agent" is used to describe a therapeutic compound or bioactive agent which treats a microbial infection, for example, an infection caused by a bacteria, virus, protozoa or fungus. The antimicrobial agent may be an antibiotic, an antifungal agent, an antiviral or an antiprotozoal or antiparasitic agent (which may also be used to treat multicellular parasites).

As used herein, the terms "antibiotic" and "antibacterial agent" refer to a chemical agent which is active against bacteria. In common usage, an antibiotic is a substance or compound (also called chemotherapeutic agent) that kills or inhibits the growth of bacteria. Anti-bacterial antibiotics can be categorized based on their target specificity: "narrow-spectrum" antibiotics target particular types of bacteria, such as Gram-negative or Gram-positive bacteria, while broad-spectrum antibiotics affect a wide range of bacteria. Antibiotics which target the bacterial cell wall (e.g., penicillins, cephalosporins, cephems), or cell membrane (e.g., polymixins), or interfere with essential bacterial enzymes (e.g., quinolones, sulfonamides) usually are bactericidal in nature. Those which target protein synthesis such as the aminoglycosides, macrolides and tetracyclines are usually bacteriostatic. Three newer classes of antibiotics include: cyclic lipopeptides (e.g., daptomycin), glycylcyclines (e.g., tigecycline), and oxazolidinones (e.g., linezolid). Tigecycline is a broad-spectrum antibiotic, while the two others are useful for Gram-positive infections.

As used herein, the term "subject" broadly refers to any animal, including but not limited to, human and non-human animals (e.g., dogs, cats, cows, horses, sheep, mammals, rodents, primates, etc.). As used herein, the term "patient" typically refers to a human subject that is being treated for a disease or condition (e.g., bacterial infection, etc.).

As used herein, the term "co-administration" refers to the administration of at least two agents or therapies to a subject. In some embodiments, the co-administration of two or more agents/therapies is concurrent. In other embodiments, the co-administration of two or more agents/therapies is sequential (e.g., a first agent/therapy is administered prior to a second agent/therapy).

DETAILED DESCRIPTION

Supramolecular structures comprising noncovalently associated peptide amphiphiles and lipids are provided. In particular, provided herein are supramolecular nanostructures of peptide amphiphiles and lipids, co-assembly of which is driven by anion-π interactions, and methods of preparation and use (e.g., as an antimicrobial agent) thereof.

In some embodiments, peptide amphiphiles described herein comprise one or more pentafluorophenylalanine (Z) residues. In some embodiments, the peptide amphiphiles described herein form β-sheets secondary structures and cylindrical fibers in water. In some embodiments, incorporation of the Z residue facilitates anion-π interactions between the peptide amphiphiles and lipids. In some embodiments, varying the position of the Z unit(s) with the peptide amphiphile(s) leads to different mechanical properties of the gels formed by the peptide amphiphiles in the presence of calcium ions and/or altered anion-π interaction strength between the amphiphiles and lipids. Experiments conducted during development of embodiments herein demonstrate that peptide amphiphiles comprising a Z residue exhibit antibacterial activity and low cytotoxicity to mammalian cells, thereby serving as an effective antimicrobial agent.

In particular, provided herein is the self-assembly of peptide amphiphiles and fatty acids driven by anion-π interactions. Peptide sequences were functionalized with a pentafluorinated phenylalanine residue (Z) to promote anion-π interactions with carboxylate headgroups of fatty acids, which were confirmed by both NMR and atomistic simulation results. It was revealed that positioning the aromatic Z unit close to the N-terminus of peptide backbones allows for strong anion-π interactions between the two components. A low content of lipid (e.g., lauric acid) results in formation of cylindrical fibers, constraining the lipid (e.g., lauric acid) within the hydrophobic core of the binary co-assemblies. Partial immigration of lipid (e.g., lauric acid) towards the hydrophilic region yields ribbon-like structures. Increasing the ratio of lipid (e.g., lauric acid) to PA leads to either formation of large vesicles by the binary systems where the anion-π interactions are strong, or a heterogeneous mixture of assemblies when the peptide amphiphiles weakly associate with the lipid (e.g., lauric acid). Experiments conducted during development of embodiments herein reveal how co-assembly involving designed specific interactions drastically change supramolecular morphology and even cross from nano to micro scales.

Experiments were conducted during development of embodiments herein to design, synthesize, and evaluate three exemplary peptide amphiphiles containing one pentafluorophenylalanine at different positions in the peptide backbones. Incorporation of the fluorinated phenyl groups that serve as electro-deficient units promotes anion-π interactions between peptide amphiphiles and fatty acids. Both experimental and computational results confirm that localizing the fluorinated aromatic unit close to the N-terminus of the peptide backbones allows for strong anion-π interactions in the binary systems, due to the preferential localization of fatty acids in the hydrophobic core of the co-assemblies. With such localized fatty acids, the binary systems co-assemble into cylindrical fibers, consistent with the morphology of the assemblies formed by peptide amphiphiles alone. However, positioning the aromatic unit in the interior of β-sheets causes partial immigration of fatty acids toward the hydrophilic region of assemblies, leading to a morphological transition from cylindrical fibers formed by the PA alone to ribbon-like structures formed by the binary system. Experiments also demonstrate that the strong association between PAs and fatty acids allows the binary systems with a large content of fatty acids to form uniform structures, while weak interactions give rise to a heterogeneous collection of assemblies. Experiments demonstrate that anion-π interactions drive binary systems co-assembling into nanostructures with various morphologies, thus offering methods to create functional supramolecular structures.

In some embodiments, the PA/lipid technology described herein improves the availability of antimicrobial peptides by increasing their synthetic yield, due to their relatively short amino acid sequences.

In some embodiments, incorporation of a negatively charged peptide sequence as hydrophilic domain into the peptide amphiphiles renders the PAs highly soluble in aqueous phase. In some embodiments, the solubility in water allows for use of the PAs described herein as drugs, without assistant delivering scaffolds.

In some embodiments, incorporation of one pentafluorophenylalanine unit (Z) as an electron-deficient aromatic group into the peptide amphiphiles at various positions allows them to interact with negatively charged components in cells, such as lipids, via anion-π interaction, thus contributing to the antibacterial activity of the peptide amphiphiles.

In some embodiments, gelation properties of the PA materials described herein are optimizable by varying PA characteristics that are understood in the field (e.g., length of lipophilic tail, identify of structural and/or charged residues, etc.) and/or described herein (e.g., number and/or location of Z residues, etc.). In some embodiments, peptide amphiphiles are gelled in the presence of calcium ions, which has implications on therapeutic delivery for example, making the gelled PAs useful as a topical antimicrobial agent to treat, for example, bacterial skin infection.

Experiments conducted during development of embodiments herein demonstrate the capacity of the peptide amphiphiles to selectively kill, for example, Staphylococcus aureus at a low concentration, while inducing negligible death of human fibroblast cells at significantly higher concentrations. In some embodiments, peptide amphiphiles are described herein that selectively kill bacteria at a low concentration and are biocompatible with mammalian cells.

In experiments conducted during development of embodiments herein, the purity and chemical structure of peptide amphiphiles described herein were characterized by high performance liquid chromatography and electrospray ionization mass spectrometry. The conformation and morphology of the assembled peptide amphiphiles were studied by circular dichroism, cryogenic transmission electron microscopy, and small-angle X-ray scattering experiments. The mechanical properties of the gel formed by the peptide amphiphiles in the presence of calcium ions was characterized by theological experiments. The critical aggregation concentration of the peptide amphiphiles in PBS buffer was determined by recording the wavelength of the maximum emission of Nile red. The association of the peptide amphiphiles with lipids, such as lauric acid, was estimated by circular dichroism, $^{19}F$ nuclear magnetic resonance spectroscopy, and isothermal titration calorimetry. The biocompatibility of the peptide amphiphiles was studied using MRC-5 human fibroblast cells. The antibacterial activity of the peptide amphiphiles was demonstrated by using Staphylococcus aureus bacterium. The absorption of the peptide amphiphiles by artificial lipid membranes was investigated by quartz-crystal microbalance-energy dissipation experiments. The structural features of artificial lipid membranes after absorbing the peptide amphiphiles was visualized by fluorescence microscopy.

In some embodiments, the peptide amphiphile molecules described herein are synthesized using preparatory techniques well-known to those skilled in the art, preferably, by standard solid-phase peptide synthesis, with the addition of a fatty acid in place of a standard amino acid at the N-terminus (or C-terminus) of the peptide, in order to create the lipophilic segment (although in some embodiments, alignment of nanofibers is performed via techniques not previously disclosed or used in the art (e.g., extrusion through a mesh screen). Synthesis typically starts from the C-terminus, to which amino acids are sequentially added using either a Rink amide resin (resulting in an —NH2 group at the C-terminus of the peptide after cleavage from the resin), or a Wang resin (resulting in an —OH group at the C-terminus). Accordingly, embodiments described herein encompasses peptide amphiphiles having a C-terminal moiety that may be selected from the group consisting of —H, —OH, —COOH, —CONH2, and —NH2.

In some embodiments, peptide amphiphiles comprise a hydrophobic (non-peptide) segment linked to a peptide. In some embodiments, the peptide comprises a structural segment (e.g., hydrogen-bond-forming segment, beta-sheet-forming segment, etc.), and a charged segment (e.g., acidic segment, basic segment, zwitterionic segment, etc.). In some embodiments, the peptide further comprises linker or spacer segments for adding solubility, flexibility, distance between segments, etc. In some embodiments, peptide amphiphiles comprise a spacer segment (e.g., peptide and/or non-peptide spacer) at the opposite terminus of the peptide from the hydrophobic segment. In some embodiments, the spacer segment comprises peptide and/or non-peptide elements. In some embodiments, the spacer segment comprises one or more bioactive groups (e.g., alkene, alkyne, azide, thiol, etc.). In some embodiments, various segments may be connected by linker segments (e.g., peptide (e.g., GG) or non-peptide (e.g., alkyl, OEG, PEG, etc.) linkers).

The lipophilic or hydrophobic segment is typically incorporated at the N- or C-terminus of the peptide after the last amino acid coupling, and is composed of a fatty acid or other acid that is linked to the N- or C-terminal amino acid through an acyl bond. In aqueous solutions, PA molecules self-assemble (e.g., into cylindrical micelles (a.k.a. nanofibers)) that bury the lipophilic segment in their core and display the bioactive peptide on the surface. In some embodiments, the structural peptide undergoes intermolecular hydrogen bonding to form beta sheets that orient parallel to the long axis of the micelle.

In some embodiments, compositions described herein comprise PA building blocks that in turn comprise a hydrophobic segment and a peptide segment. In certain embodiments, a hydrophobic (e.g., hydrocarbon and/or alkyl/alkenyl/alkynyl tail, or steroid such as cholesterol) segment of sufficient length (e.g., 2 carbons, 3 carbons, 4 carbons, 5 carbons, 6 carbons, 7 carbons, 8 carbons, 9 carbons, 10 carbons, 11 carbons, 12 carbons, 13 carbons, 14 carbons, 15 carbons, 16 carbons, 17 carbons, 18 carbons, 19 carbons, 20 carbons, 21 carbons, 22 carbons, 23 carbons, 24 carbons, 25 carbons, 26 carbons, 27 carbons, 28 carbons, 29 carbons, 30 carbons or more, or any ranges there between.) is covalently coupled to peptide segment (e.g., a peptide comprising a segment having a preference for beta-strand conformations or other supramolecular interactions) to yield a peptide amphiphile molecule.

In some embodiments, a plurality of such PAs will self-assemble in water (or aqueous solution) into a nanostructure (e.g., nanofiber). In various embodiments, the relative lengths of the peptide segment and hydrophobic segment result in differing PA molecular shape and nanostructural architecture. For example, a broader peptide segment and narrower hydrophobic segment results in a generally conical molecular shape that has an effect on the assembly of PAs (See, e.g., J. N. Israelachvili Intermolecular and surface forces: 2nd ed.; Academic: London San Diego, 1992; herein incorporated by reference in its entirety). Other molecular shapes have similar effects on assembly and nanostructural architecture.

In some embodiments, to induce self-assembly of an aqueous solution of peptide amphiphiles, the pH of the solution may be changed (raised or lowered) or multivalent ions, such as calcium, or charged polymers or other macromolecules may be added to the solution.

In some embodiments, the hydrophobic segment is a non-peptide segment (e.g., alkyl/alkenyl/alkynyl group). In some embodiments, the hydrophobic segment comprises an alkyl chain (e.g., saturated) of 4-25 carbons (e.g., 4, 5, 6, 7, 8, 9, 10, 11, 12, 13, 14, 15, 16, 17, 18, 19, 20, 21, 22, 23, 24, 25), fluorinated segments, fluorinated alkyl tails, heterocyclic rings, aromatic segments, pi-conjugated segments, cycloalkyls, oligothiophenes etc. In some embodiments, the hydrophobic segment comprises an acyl/ether chain (e.g., saturated) of 2-30 carbons (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30).

In some embodiments, PAs comprise one or more peptide segments. Peptide segment may comprise natural amino acids, modified amino acids, unnatural amino acids, amino acid analogs, peptidomimetics, or combinations thereof. In some embodiments, peptide segment comprise at least 50% sequence identity or similarity (e.g., conservative or semi-conservative) to one or more of the peptide sequences described herein.

In some embodiments, peptide amphiphiles comprise a charged peptide segment. The charged segment may be acidic, basic, or zwitterionic.

In some embodiments, peptide amphiphiles comprise an acidic peptide segment. For example, in some embodiments, the acidic peptide comprises one or more (e.g., 1, 2, 3, 4, 5, 6, 7, or more) acidic residues (D and/or E) in sequence. In some embodiments, the acidic peptide segment comprises up to 7 residues in length and comprises at least 50% acidic residues. In some embodiments, an acidic peptide segment comprises $(Xa)_{1-7}$, wherein each Xa is independently D or E. In some embodiments, an acidic peptide segment comprises EE.

In some embodiments, peptide amphiphiles comprise a basic peptide segment. For example, in some embodiments, the acidic peptide comprises one or more (e.g., 1, 2, 3, 4, 5, 6, 7, or more) basic residues (R. H. and/or K) in sequence. In some embodiments, the basic peptide segment comprises up to 7 residues in length and comprises at least 50% basic residues. In some embodiments, an acidic peptide segment comprises $(Xb)_{1-7}$, wherein each Xb is independently R, H, and/or K.

In some embodiments, peptide amphiphiles comprises a structural and/or beta-sheet-forming segment. In some embodiments, the structural segment is rich in H, I, L, F, V, and A residues. In some embodiments, the structural and/or beta-sheet-forming segment comprises an alanine- and valine-rich peptide segment (e.g., AAVV (SEQ ID NO: 18), AAAVVV (SEQ ID NO: 19), or other combinations of V and A residues, etc.). In some embodiments, the structural and/or beta sheet peptide comprises 4 or more consecutive A and/or V residues, or conservative or semi-conservative substitutions thereto. In some embodiments, the structural and/or beta-sheet forming peptide segment comprises 4 or more consecutive non-polar aliphatic residues (e.g., alanine (A), valine (V), leucine (L), isoleucine (I), methionine (M)). In some embodiments, the structural and/or beta-sheet forming peptide segment comprises 2-16 amino acids in length and comprises 4 or more (e.g., 2, 3, 4, 5, 6, 7, 8, 9, 10, 11, 12, 13, 14, 15, 16, or ranges there between) non-polar aliphatic residues.

In some embodiments, peptide amphiphiles comprise a non-peptide spacer or linker segment. In some embodiments, the non-peptide spacer or linker segment is located at the opposite terminus of the peptide from the hydrophobic segment. In some embodiments, the spacer or linker segment provides the attachment site for a bioactive group. In some embodiments, the spacer or linker segment provides a reactive group (e.g., alkene, alkyne, azide, thiol, maleimide etc.) for functionalization of the PA. In some embodiments, the spacer or linker is a substantially linear chain of CH2, O, $(CH_2)_2O$, $O(CH_2)_2$, NH, and C=O groups (e.g., CH2(O $(CH_2)_2)_2NH$, $CH2(O(CH_2)_2)_2NHCO(CH_2)_2CCH$, etc.). In some embodiments, a spacer or linker further comprises additional bioactive groups, substituents, branches, etc.

Suitable peptide amphiphiles for use in the materials herein, as well as methods of preparation of PAs and related materials, amino acid sequences for use in PAs, and materials that find use with PAs, are described in the following patents: U.S. Pat. Nos. 9,044,514; 9,040,626; 9,011,914; 8,772,228; 8,748,569 8,580,923; 8,546,338; 8,512,693; 8,450,271; 8,236,800; 8,138,140; 8,124,583; 8,114,835; 8,114,834; 8,080,262; 8,076,295; 8,063,014; 7,851,445; 7,838,491; 7,745,708; 7,683,025; 7,554,021; 7,544,661; 7,534,761; 7,491,690; 7,452,679; 7,371,719; 7,030,167; all of which are herein incorporated by reference in their entireties.

The characteristics (e.g., shape, rigidity, hydrophilicity, etc.) of a PA supramolecular structure depend upon the identity of the components of a peptide amphiphile (e.g., lipophilic segment, acidic segment, structural segment, bioactive segment, etc.). For example, nanofibers, nanospheres, intermediate shapes, and other supramolecular structures are achieved by adjusting the identity of the PA component parts. In some embodiments, characteristics of supramolecular nanostructures of PAs are altered by post-assembly manipulation (e.g., heating-cooling, stretching, etc.).

In some embodiments, a peptide amphiphile comprises: (a) a hydrophobic tail comprising an alkyl chain of 8-24 carbons: (b) a structural segment (e.g., comprising VVAA (SEQ ID NO: 8), VVVAAA (SEQ ID NO: 7), etc.); and (c) a charged segment (e.g., comprising KK, EE, EEE, etc). In some embodiments, any PAs within the scope described herein, comprising the components described herein, or within the skill of one in the field, may find use herein.

In some embodiments, peptide amphiphiles comprise a bioactive moiety. In particular embodiments, a bioactive moiety is the C-terminal or N-terminal most segment of the PA. In some embodiments, the bioactive moiety is attached to the end of the charged segment. In some embodiments, the bioactive moiety is exposed on the surface of an assembled PA structure (e.g., nanofiber). A bioactive moiety is typically a peptide, but is not limited thereto. In some embodiments, a bioactive moiety is a peptide sequence that binds a peptide or polypeptide of interests. Bioactive peptides and other moieties for achieving functionality will be understood.

In some embodiments, a peptide amphiphile comprises: (a) a hydrophobic tail comprising an alkyl chain of 8-24 carbons; (b) a structural segment (e.g., comprising VVAA (SEQ ID NO: 8). AAVV (SEQ ID NO: 18), VA, AV, VVVAAA (SEQ ID NO: 7), etc.): (c) a charged segment (e.g., comprising KK, EE, EK, KE, etc.), and a bioactive peptide. In some embodiments, a PA further comprises an attachment segment or residue (e.g., K) for attachment of the hydrophobic tail to the peptide portion of the PA. In some embodiments, the hydrophobic tail is attached to a lysine side chain.

In some embodiments, a peptide amphiphile comprises (e.g., from C-terminus to N-terminus or from N-terminus to C-terminus): bioactive peptide—charged segment (e.g., comprising KK, EE, EK, KE, EEE, etc.)—structural segment (e.g., comprising VVAA (SEQ ID NO: 8), AAVV (SEQ ID NO: 18), VA, AV, VVVAAA (SEQ ID NO: 7), etc.)-hydrophobic tail (e.g., comprising an alkyl chain of 8-24 carbons).

In some embodiments, a peptide amphiphile comprises (e.g., from C-terminus to N-terminus or from N-terminus to C-terminus): bioactive peptide—charged segment (e.g., comprising KK, EE, EK, KE, EEE, etc.)—structural segment (e.g., comprising VVVAAA (SEQ ID NO: 7), VVAA (SEQ ID NO: 8), AAVV (SEQ ID NO: 18), VA. AV, etc.)-attachment segment or peptide (e.g., K)—hydrophobic tail (e.g., comprising an alkyl chain of 8-24 carbons).

In some embodiments, the peptide amphiphiles described herein comprise one or more (e.g., 1, 2, 3, 4, 5, 6, 7, 8, or more, or ranges therebetween) pentafluorophenylalanine residues (Z). In some embodiments, the peptide amphiphiles described herein comprise one, but not more than one, pentafluorophenylalanine residue (Z). In some embodiments, a pentafluorophenylalanine residue is of the chemical formula:

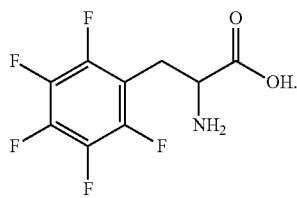 [SMILES: NC(Cc1c(F)c(F)c(F)c(F)c1F)C(=O)O]

In some embodiments, pentafluorophenylalanine is indicated herein by "Z." In some embodiments, a Z residue is located in the peptide portion of the peptide amphiphile. In some embodiments, a Z residue is located in the structural, charged, or bioactive portion of the peptide amphiphile. In some embodiments, a Z residue is located in the structural or charged. In some embodiments, a residue within a known PA structural sequence is substituted with a Z residue (e.g., comprising ZVVAAA (SEQ ID NO: 1), VZVAAA (SEQ ID NO: 2), VVZAAA (SEQ ID NO: 3), VVVZAA (SEQ ID NO: 4), VVVAZA (SEQ ID NO: 5), or VVVAAZ (SEQ IS NO: 6), ZVAA (SEQ ID NO: 20), VZAA (SEQ ID NO: 21), VVZA (SEQ ID NO: 22). VVAZ (SEQ ID NO: 23), etc.). In some embodiments, a residue within a known PA charged sequence is substituted with a Z residue (e.g., comprising ZEE (SEQ ID NO: 31), EZE (SEQ ID NO: 32), EEZ (SEQ ID NO: 33), ZKK, KZK, KKZ, ZEKK (SEQ ID NO: 24), EZKK (SEQ ID NO: 25), EEZK (SEQ ID NO: 26), EEKZ (SEQ ID NO: 27), etc.). In some embodiments, any residue in a suitable peptide amphiphile may be substituted for a Z residue.

In some embodiments, compositions herein comprise a supramolecular complex of peptide amphiphiles and lipids. In some embodiments, the lipid moiety is selected from the group consisting of: a phospholipid, a glyceride, a sphingolipid, an eicosanoid, and a fatty acid. In some embodiments, a lipid comprises one or more fatty acid chains, selected from a short chain fatty acid (carbon chain of <6 carbons (e.g., formic acid, acetic acid, propionic acid, butyric acid, isobutyric acid, valeric acid, isovaleric acid, etc.)), a medium chain fatty acid (carbon chain of 6-12 carbons (e.g., caproic acid, caprylic acid, capric acid, lauric acid, etc.)), a long chain fatty acid (carbon chain of 13-21 carbons (e.g., myristic acid, palmitic acid, stearic acid, arachidic acid, etc.)), a very long chain fatty acid (carbon chain of >21 carbons (e.g., behenic acid, lignoceric acid, cerotic acid etc.)), and/or any suitable combinations thereof.

In some embodiments, lipids that find use in embodiments herein are fatty acids. In some embodiments, fatty acids in the compositions herein are a short chain fatty acid (carbon chain of <6 carbons (e.g., formic acid, acetic acid, propionic acid, butyric acid, isobutyric acid, valeric acid, isovaleric acid, etc.)), a medium chain fatty acid (carbon chain of 6-12 carbons (e.g., caproic acid, caprylic acid, capric acid, lauric acid, etc.)), a long chain fatty acid (carbon chain of 13-21 carbons (e.g., myristic acid, palmitic acid, stearic acid, arachidic acid, etc.)), a very long chain fatty acid (carbon chain of >21 carbons (e.g., behenic acid, lignoceric acid, cerotic acid, etc.)), and/or any suitable combinations thereof. In some embodiments, the acyl chain portion of the fatty acid comprises $C_6$-$C_{24}$ (e.g., $C_6$, $C_8$, $C_{10}$, $C_{12}$, $C_{14}$, $C_{16}$, $C_{18}$, $C_{20}$, $C_{22}$, $C_{24}$, or ranges therebetween). In some embodiments, the length of the fatty acid corresponds to the length of the lipophilic tail of the peptide amphiphile (e.g., within 6 carbons in length, within 4 carbons in length, within 2 carbons in length, within 1 carbons in length, same length). In some embodiments, the length of the fatty acid is unrelated to the length of the lipophilic tail of the peptide amphiphile. In some embodiments, a composition may comprise multiple different lipids or multiple different lengths. In some embodiments, a single lipid species is present (other than in the PA tail).

In some embodiments, the lipid is a saturated fatty acid selected from caprylic acid, capric acid, lauric acid, myristic acid, palmitic acid, stearic acid, arachidic acid, behenic acid, lignoceric acid, and cerotic acid.

In some embodiments, the lipid is a saturated fatty acid selected from myristoleic acid, palmitoleic acid, sapienic acid, oleic acid, elaidic acid, vaccenic acid, linoleic acid, linoelaidic acid, α-linolenic acid, arachidonic acid, eicosapentaenoic acid, erucic acid, and docosahexaenoic acid.

In some embodiments, the PA tail and the lipid are both lauric acid.

In some embodiments, the ratio of PA to lipid is between 0.1:1 and 1:0.1 (e.g., 0.1:1, 0.2:1, 0.3:1, 0.4:1, 0.5:1, 0.6:1, 0.7:1, 0.8:1, 0.9:1, 1:1, 1:0.9, 1:0.9, 1:0.9, 1:0.9, 1:0.9, 1:0.9, 1:0.9, 1:0.9, or ranges therebetween (e.g., 1:0.2 to 0.8:1)).

In some embodiments, compositions comprising supramolecular complexes of pentafluorophenylalanine-containing PAs and lipids are provided. In some embodiments, such supramolecular complexes find use in the treatment or prevention of bacterial infection. In some embodiments, supramolecular complexes described herein find use in the treatment of infections by Gram-positive microorganism, Gram-negative microorganism, and antibiotic-resistant strains, etc. In some embodiments, supramolecular complexes described herein find use in the treatment of microorganisms such as Streptococcus, Streptococcus Pneumonia, Corynebacterium diphtheriae, Clostridium tetani, Bacillus anthracis, Streptomyces griseus, Staphylococcus aureus, Bacillus subtilis, Salmonella, shigella, typhoid bacillus, Vibrio cholerae, Yersinia pestis, Neisseria gonorrhoeae, Neisseria meningitidis, Spirochaeta, Escherichia coli, and Pseudomonas aeruginosa, and antibiotic-resistant strains thereof. Embodiments herein find use in the treatment of infections by a wide-range of bacteria and microorganisms and are not limited to those listed above.

In some embodiments, the molecular complexes of pentafluorophenylalanine-containing PAs and lipids described herein find use in the treatment of a wide range of infections, such as bacterial skin infections (e.g., cellulitis, folliculitis, impetigo, etc.), foodborne bacterial infections (e.g., Campylobacter jejuni, Escherichia coli, Clostridium botulinum, Listeria monocytogenes, Salmonella, etc.), sexually transmitted bacterial infections (e.g., chlamydia, gonorrhea, syphilis, bacterial vaginosis, etc.), bacterial meningitis, ear infections, urinary tract infections, respiratory tract infections, sinus infections, wound infections, surgical site infections, etc.

In some embodiments, the molecular complexes of pentafluorophenylalanine-containing PAs and lipids described herein are administered with other agents in a combination therapy, for example with other antibacterial agents, such as, cephalosporin antibiotics (cephalexin, cefuroxime, cefadroxil, cefazolin, cephalothin, cefaclor, cefamandole, cefoxitin, cefprozil, and ceftobiprole); fluoroquinolone antibiotics (cipro, Levaquin, floxin, tequin, avelox, and norflox); tetracycline antibiotics (tetracycline, minocycline, oxytetracycline, and doxycycline); penicillin antibiotics (amoxicillin, ampicillin, penicillin V, dicloxacillin, carbenicillin, vancomycin, and methicillin); and carbapenem antibiotics (ertapenem, doripenem, imipenem/cilastatin, and meropenem).

In some embodiments, provided herein are pharmaceutical compositions comprising the PA/lipid complexes described herein and a pharmaceutically acceptable carrier. Any carrier which can supply an active agent is a suitable carrier, and such carriers are well known in the art. In some embodiments, compositions are formulated for administration by any suitable route, including but not limited to, orally (e.g., such as in the form of tablets, capsules, granules or powders), sublingually, bucally, parenterally (such as by subcutaneous, intravenous, intramuscular, intradermal, or intrasternal injection, or infusion) (e.g., as sterile injectable aqueous or non-aqueous solutions or suspensions)), nasally (including administration to the nasal membranes, such as by inhalation spray), topically (such as in the form of a cream or ointment), transdermally (such as by transdermal patch), or rectally (such as in the form of suppositories), etc. In some embodiments, pharmaceutical compositions are delivered to the patient systemically or locally.

A pharmaceutical composition may be administered in the form which is formulated with a pharmaceutically acceptable carrier and optional excipients, adjuvants, etc. in accordance with good pharmaceutical practice. The pharmaceutical composition may be in the form of a solid, semi-solid or liquid dosage form: such as powder, solution, elixir, syrup, suspension, cream, drops, paste and spray. As those skilled in the art would recognize, depending on the chosen route of administration (e.g. pill, injection, etc.), the composition form is determined. In general, it is preferred to use a unit dosage form in order to achieve an easy and accurate administration of the active pharmaceutical peptide or polypeptide. In general, the therapeutically effective pharmaceutical agent (e.g., PA/lipid complexes described herein) is present in such a dosage form at a concentration level ranging from about 0.5% to about 99% by weight of the total composition, e.g., in an amount sufficient to provide the desired unit dose. In some embodiments, the pharmaceutical composition may be administered in single or multiple doses. The particular route of administration and the dosage regimen will be determined by one of skill in keeping with the condition of the individual to be treated and said individual's response to the treatment. The amount of the active ingredient (e.g., PA/lipid complexes described herein) that may be combined with such materials to produce a single dosage form will vary depending upon various factors, as indicated above. A variety of materials can be used as carriers, adjuvants and vehicles in the composition of the invention, as available in the pharmaceutical art.

In some embodiments, pharmaceutical compositions (e.g., comprising PA/lipid complexes described herein) are co-administered (concurrently or in series) with one or more additional therapeutic agents. Additional therapeutic agents may comprise other antimicrobials (e.g., antibiotics, antifungals, antiparasitic, antiviral, etc.). In some embodiments, co-administered agents are co-formulated. In other embodiments, the agents are separately formulated. Co-administration may occur concurrently or sequentially. For concurrent administration, the agents may be co-formulated or separately formulated. In some embodiments, the agents are administered by the same route or by separate routes of administration. For sequential administration, any suitable time lapse may occur between administrations, for example, 1 minute, 2 minutes, 5 minutes, 10 minutes, 30 minutes, 1 hour, 2 hours, 4 hours, 6 hours, 8 hours, 12 hours, 24 hours, 48 hours, 72 hours, 1 week, 2 weeks, 4 weeks, or more, or ranges there between.

In some embodiments, pharmaceutical compositions (e.g., comprising PA/lipid complexes described herein) are provided as part of a kit (e.g., comprising other therapeutic agents, packaging, container(s), instructions, devices for administration, etc.).

In some embodiments, pharmaceutical compositions and/or kits for administration/co-administration comprise a PA/lipid complexes described herein and one or more therapeutic agents.

In some embodiments, the PA/lipid complexes described herein is co-administered with one or more antibiotics. In some embodiments, such formulations/co-administrations are useful in the treatment/prevention of multiple types of pathogenic infections. In some embodiments, the antibiotic may inhibit cell wall synthesis, protein synthesis, nucleic acid synthesis, or alter cell membrane function. Classes of antibiotics that find use in conjunction with the other embodiments herein include, but are not limited to, macrolides (i.e., erythromycin), penicillins (i.e., nafcillin), cephalosporins (i.e., cefazolin), carbepenems (i.e., imipenem, aztreonam), other beta-lactam antibiotics, beta-lactam inhibitors (i.e., sulbactam), oxalines (i.e. linezolid), aminoglycosides (i.e., gentamicin), chloramphenicol, sulfonamides (i.e., sulfamethoxazole), glycopeptides (i.e., vancomycin), quinolones (i.e., ciprofloxacin), tetracyclines (i.e., minocycline), fusidic acid, trimethoprim, metronidazole, clindamycin, mupirocin, rifamycins (i.e., rifampin), streptogramins (i.e., quinupristin and dalfopristin) lipoprotein (i.e., daptomycin), polyenes (i.e., amphotericin B), azoles (i.e., fluconazole), and echinocandins (i.e., caspofungin acetate). Examples of specific antibiotics that can be used include, but are not limited to, erythromycin, nafcillin, cefazolin, imipenem, aztreonam, gentamicin, sulfamethoxazole, vancomycin ciprofloxacin, trimethoprim, rifampin, metronidazole, clindamycin, teicoplanin, mupirocin, azithromycin, clarithromycin, ofloxacin, lomefloxacin, norfloxacin, nalidixic acid, sparfloxacin, pefloxacin, amifloxacin, gatifloxacin, moxifloxacin, gemifloxacin, enoxacin, fleroxacin, minocycline, linezolid, temafloxacin, tosufloxacin, clinafloxacin, sulbactam, clavulanic acid, amphotericin B, fluconazole, itraconazole, ketoconazole, and nystatin.

In some embodiments, the PA/lipid complexes described herein are co-administered with one or more beneficial and/or probiotic bacteria. In some embodiments, such formulations/co-administrations are useful in the treatment/prevention of multiple types of pathogenic infection and/or for establishing/restoring/maintaining normal microbiota. Any beneficial and/or probiotic bacteria may find use in embodiments herein.

In some embodiments, the PA/lipid complexes described herein are co-administered with one or more antiviral agents or treatments In some embodiments, the PA/lipid complexes described herein are co-administered with a topical antifungal, such as clotrimazole, econazole, ketoconazole, miconazole, tioconazole, terbinafine, and amorolfine. Such agents may be administered as creams, shampoos, soaps, liquids, sprays, etc. and may be co-formulated with the PA/lipid complexes described herein or may be separately formulated. In some embodiments, PA/lipid complexes described herein are co-administered with an oral antifungal, such as miconazole, nystatin, terbinafine, itraconazole, fluconazole, posaconazole, and voriconazole. Such agents may be administered oral gels, liquids, pills, capsules, tablets, etc. and may be co-formulated with the PA/lipid complexes described herein or may be separately formulated. In some embodiments, PA/lipid complexes described herein are co-administered with an antifungal injection, such as amphotericin, flucytosine, itraconazole, voriconazole, anidulafungin, caspofungin, and micafungin.

Any suitable formulations or co-formulations (with the PA/lipid complexes described herein) of the aforementioned agents may find use in embodiments herein. In the case of separate formulation, the PA/lipid complexes described herein and the other agents may be administered by the same route or my separate routes of administration.

All publications and patents listed below and/or provided herein are incorporated by reference in their entireties. Various modifications and variations of the described compositions and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the present invention.

EXPERIMENTAL

Example 1

Methods
Bacterial Cell Culture

S. aureus (ATCC 25923) (American Type Culture Collection, Manassas, Va.) was cultured in LB broth overnight at 37° C. The suspension of the overnight culture was inoculated in fresh LB broth and cultured under aerobic conditions until reaching an $OD_{600}$ value of approximately 0.5 (exponential growth phase). The bacterial cells were harvested by centrifugation at 1,500×g for 10 min, washed thrice with PBS, and re-suspended in the appropriate solution for experiment. The bacterial cell suspensions were diluted to an $OD_{600}$ value of 0.1, which corresponds to $1 \times 10^7$ CFU/mL for S. aureus. Before experiment, the bacterial cells were then diluted 1:10 with PBS unless otherwise noted.

Minimum Inhibitory Concentration (MIC) Testing

The MIC value is the lowest concentration of test agent that completely inhibits visible growth of a bacterium. The MIC values of peptide amphiphiles were determined in PBS. The MIC determination was made by the Mueller-Hinton (MH) agar plate method. Two-fold serial dilutions of test compound (peptide amphiphiles) solutions in PBS were firstly made in a 96-well microtiter plate. The test compound concentration ranged from 500 μM to 1 μM with 50 μL volume. Then, 50 μL of S. aureus ($1 \times 10^6$ CFU/mL) suspended in PBS was added to each well for a final cell density of $5 \times 10^5$ CFU/mL. The samples were incubated for 3 hrs at 37° C., and then streaked onto MH agar plates. The plates were incubated overnight at 37° C. and the MIC value was recorded based on the lowest test compound concentration that inhibited colony growth.

Minimum Bactericidal Concentration (MBC) Testing

The MBC value is the minimal amount of test agent that results in a 99.9% decrease in the number of infectious bacterium within the initial inoculum within 24 hrs in a standard test. Bacterial cells were cultured overnight 3-4% (v/v) in fresh media (LB media 5 mL and 200 μL of bacterial solution). The overnight culture was resuspended in fresh LB media (5 mL and 200 μL of the overnight culture) in order to yield an $OD_{600}$ value of ~0.5 (~$10^8$ CFU/mL). The bacteria were then washed thrice with PBS and resuspended in order to yield an $OD_{600}$ value of 0.1. The bacterial solution was then diluted to ~$10^6$ CFU/mL (40× dilution), 100 μL of the ~$10^6$ CFU/mL suspension was incubated with 100 μL of 2-time serially diluted peptide amphiphile stocks in PBS from 31 μM to 0.24 μM at 37° C. for 3 hrs. The final inoculum was ~$5 \times 10$ CFU/mL. After incubation, 100 μL of the incubated sample from each well was diluted $10^1$ to $10^5$ in PBS and then 10 μL of each diluted sample was streaked onto MH agar plates. All samples were tested in duplicate. All streaked MH agar plates were incubated at 37° C. for 24 hrs and the colonies were counted manually.

Bacterial Live-Dead Assay

S. aureus cells (ATCC 25923) were overnight cultured in LB media. Next day, 2×00 uL of the overnight culture was resuspended in 5 mL of fresh LB media and incubated until an $OD_{600}$ value of 0.5-0.6 was reached. Bacterial cells were washed 3 times with PBS and resuspended in fresh PBS in order to yield an $2 \times 10^8$ CFU/mL inoculum, 200 μL of the bacterial solution was incubated with 200 μL of PBS buffer containing peptide Z1 (400, 200, and 100 μM) in a 48-well plate at 37° C. for 3 hrs. Bacteria in PBS (no peptide amphiphiles) served as a negative control. After the incubation, a dye mixture (Syto 9/PI; LIVE/DEAD BacLight Bacterial Viability Kit from Molecular Probes, Eugene, Oreg.) was added to each well and the samples were incubated at room temperature on a shaker for 20 minutes in the dark. Next, 10 μL of the stained bacterial suspensions were transferred onto a slide and observed in a fluorescence microscope.

Human Fibroblast Cell Cytotoxicity

Human MRC-5 fibroblasts were cultured in Alpha MEM (HyClone) medium supplemented with 10% fetal bovine serum (FBS) and 1% Penicillin/Streptomycin at 37° C. under 5% $CO_2$. The cells were plated into a 96-well tissue culture plate at a density of 5,000 cells per well, and incubated at 37° C. under 5% $CO_2$. After 24 hrs, the medium was discarded and the cells were treated with peptide amphiphiles that were prepared as a series of eight two-fold dilutions in cell medium (4 µM—500 µM). Cells in medium (no agent added) were used as a negative control. Triton X-100 (1%) was used to achieve 100% of cell cytotoxicity (positive control). The cells were incubated with test agent at 37° C. under 5% $CO_2$ for 24 hours. After incubation, cell viability was determined with Cell Counting Kit-8 (CCK-8; Dojindo). After 24 hrs exposure to the peptide amphiphiles, the cells were incubated with 10% CCK-8 solution (200 µL per well) containing water-soluble tetrazolium salt (WST-8) at 37° C. under 5% $CO_2$ for 90 minutes. The absorbance was measured at 450 nm using a microplate reader (Infinite M200 Pro, Tecan Group Ltd.). All data were presented as the mean value±standard deviation (SD). The significance was determined using unpaired, two-tailed Student's t-test.cell viability was determined with CCK-8 kit.

Human Keratinocyte Cell Cytotoxicity

HaCaT cells (human keratinocytes) were seeded onto a 96-well tissue culture plate at a density of 20,000 cells per well in DMEM High Glucose medium supplemented with 10% FBS and 1% Streptomycin/Amphotericin B/Penicillin. The peptide amphiphiles samples were diluted with medium to 0.5 mM. Two-fold dilution series of the solutions in cell medium were prepared. After removing the medium, solutions were added to the cells, and the plate was incubated for 24 hours at 37° C. Cells in medium were used as a negative control. Triton X-100 at conc. 1% was used to achieve 100% of cell cytotoxicity (positive control). Cell viability was determined with CCK-8 kit. The cells were incubated with CCK-8 solution containing WST-8* for 90 minutes. Principle of the method: WST-8 is reduced by dehydrogenases in the cells, giving formazan, which was detected with spectrometer at 450 nm. Viability of the cells was calculated as a percentage of the cells that remained live after incubation with the samples. The significance was determined using unpaired, two-tailed Student's t-test.

Results Experiments conducted during development of embodiments herein employed exemplary peptide amphiphiles and fatty acids as the two components that associate, primarily driven by anion-π interactions. Peptide amphiphiles (PAs) containing an amino acid sequence substituted by an alkyl chain can form nanostructures with a variety of morphologies in water, mostly depending on their primary structure (refs, 28-31; incorporated by reference in their entireties). Fatty acids assemble into a rich variety of supramolecular architectures driven by electrostatic interactions and hydrophobic effects (ref. 32-33; incorporated by reference in its entirety). Lauric acid was used in exemplary embodiments, due to its relatively high solubility in water and the possibility of matching its 12 carbon alkyl tail to those used commonly in peptide amphiphiles: although other lipids and other PA tail lengths (e.g., matching or not matching) find use in embodiments herein. One fluorinated phenylalanine residue (Z: ref. 35; incorporated by reference in its entirety) was incorporated, as an electro-deficient amino acid, into a VVVAAAEEE (SEQ ID NO: 28) peptide sequence of a PA. The Z amino acid replaced one V residue in different positions, hence the nomenclature of PAs Z1, Z2, and Z3 (FIG. 1A). It was contemplated that the alkyl tail of lauric acid would be buried within the hydrophobic core of supramolecular structures formed and therefore varying the position of the Z residue would allow optimization the relative distance between the fluorinated aromatic groups of the PA and carboxyl acid headgroups of the lipid, which would in turn maximize anion-π interactions between PA molecules and lauric acid.

Figure 1B:
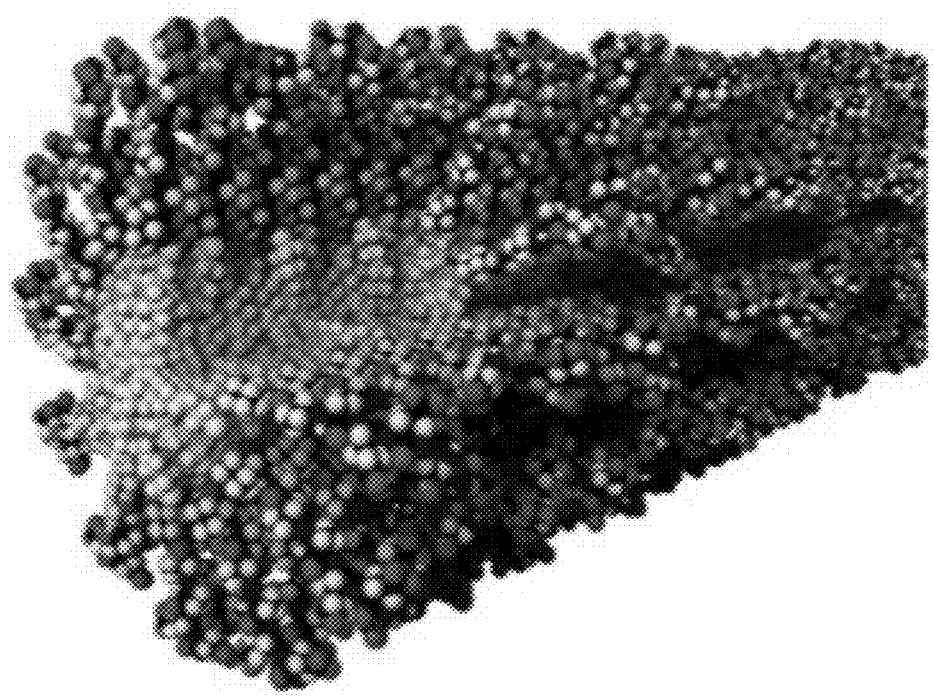
(FIG. 1B) Circular dichroism spectra of PA Z1, PA Z2, PA Z3, and the parent PA in water (50 µM) at 25° C.
Figure 1C:
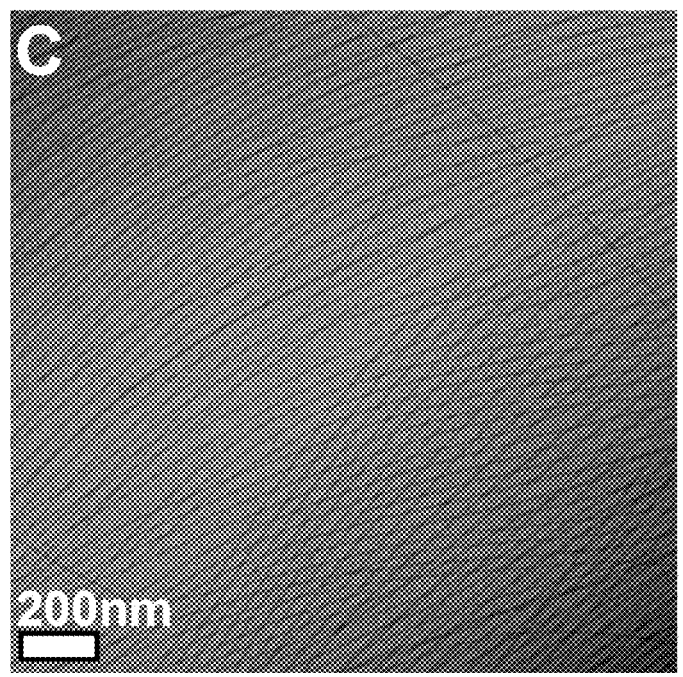
(FIG. 1C) Representative cryo-TEM image of cylindrical fibers formed by PA Z1.
Figure 1D:
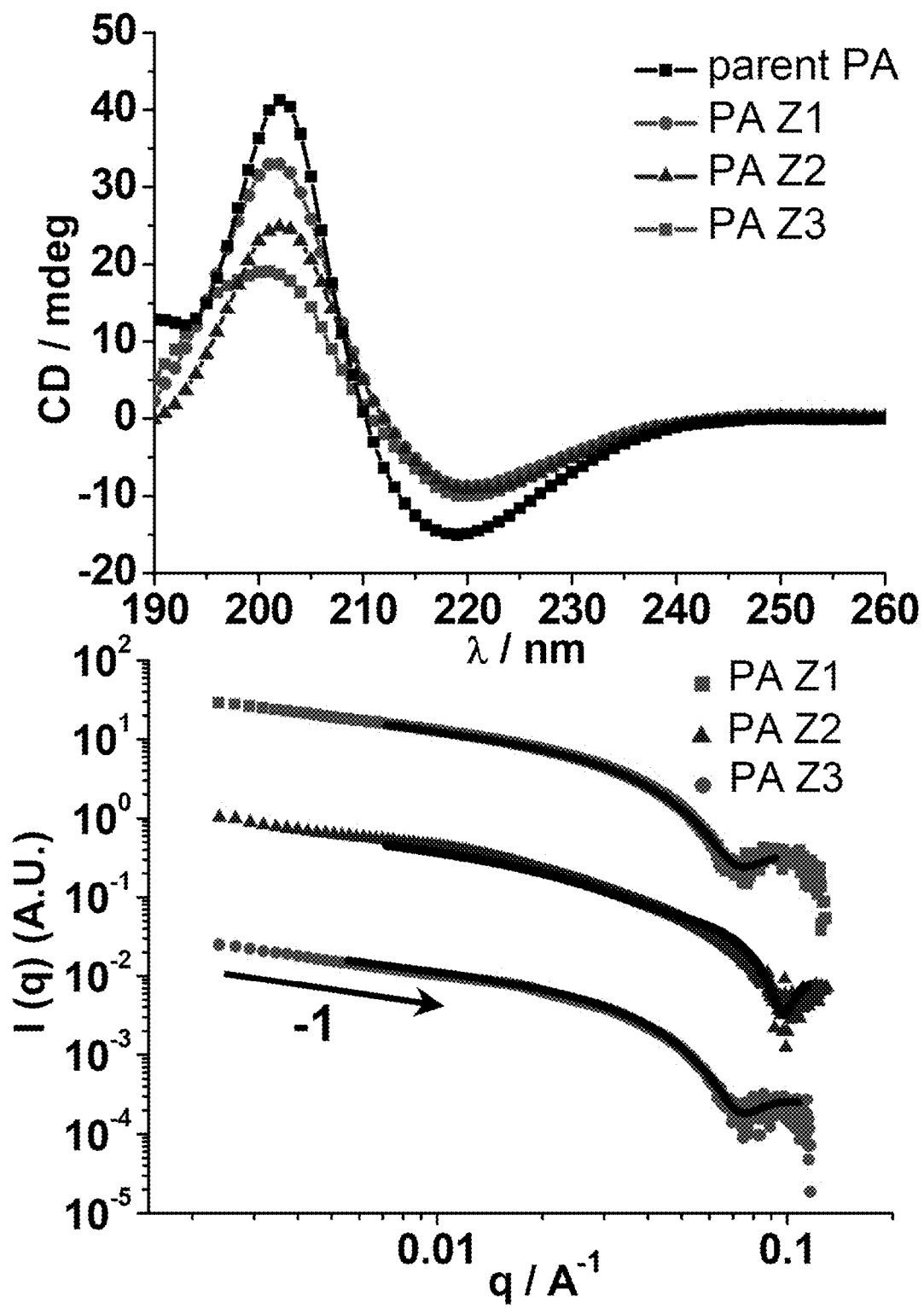
(FIG. 1D) SAXS profiles of the PA solutions displaying the scattered intensity versus the scattering vector q (log-log plot) in water. Scattering intensities are offset vertically for clarity and the fitting curves for the scattering data are shown in black.

To establish the position-dependent effects of the Z residue on supramolecular morphology, the self-assembly behavior of the PAs was examined alone in water by circular dichroism (CD) spectroscopy, cryogenic transmission electron microscopy (cryo-TEM), and small-angle x-ray scattering (SAXS). Similar to the canonical PA that lacks the Z residue (ref. 36; incorporated by reference in its entirety), D spectroscopic measurements showed that PA Z1, Z2, and Z3 all adopted predominantly β-sheet secondary structure in solution (FIG. 1B), indicating that β-sheet hydrogen bonds are still be formed among amino acid sequences that contain a fluorinated aromatic unit. In terms of morphology, well-defined cylindrical nanofibers with a 7-10 nm diameter were formed by all three PAs in aqueous solution as observed by cryo-TEM (FIG. 1C). The morphology of the PA assemblies was also confirmed by SAXS scattering experiments. The scattering signals showed an approximately −1 slope in the low-q region for all the PAs, supporting the cryo-TEM observation of cylindrical nanofibers as the dominant morphology (see FIG. 1D). The diameter of the one-dimensional filaments was estimated to be approximately 8 nm, as determined by fitting the scattering curves to a core-shell cylinder model. Collectively, these results demonstrate that all the designed PAs form well-defined one-dimensional nanostructures in water, in spite of the presence of the Z residue in the peptide sequence. The Z residue would be expected to contribute to steric interactions within the β-sheets in the internal structure of the supramolecular filaments, but these experiments demonstrate that it does not disrupt the self-assembly behavior of this group of PA molecules.

Figure 2A:
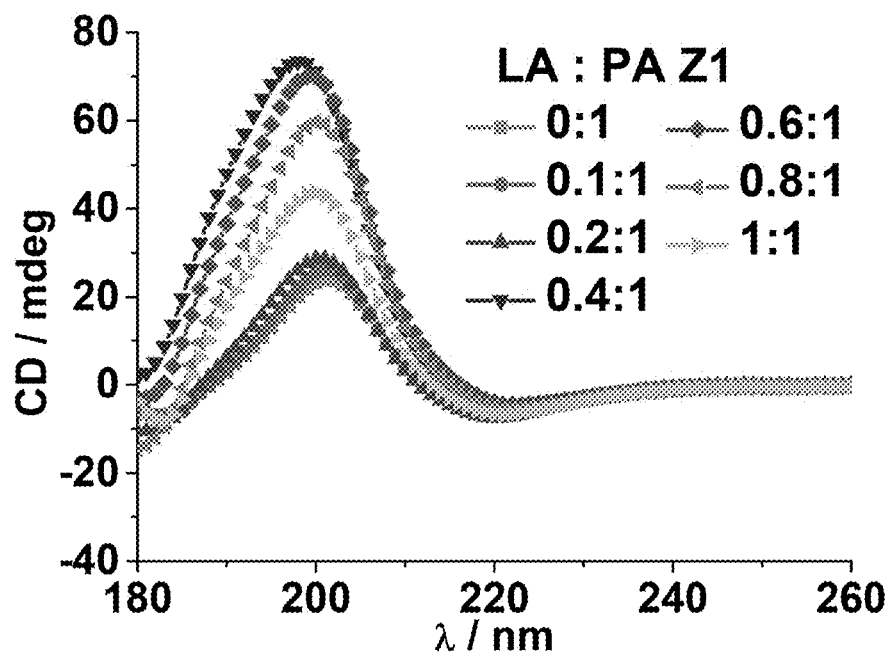
FIGS. 2A-F.
Figure 2B:
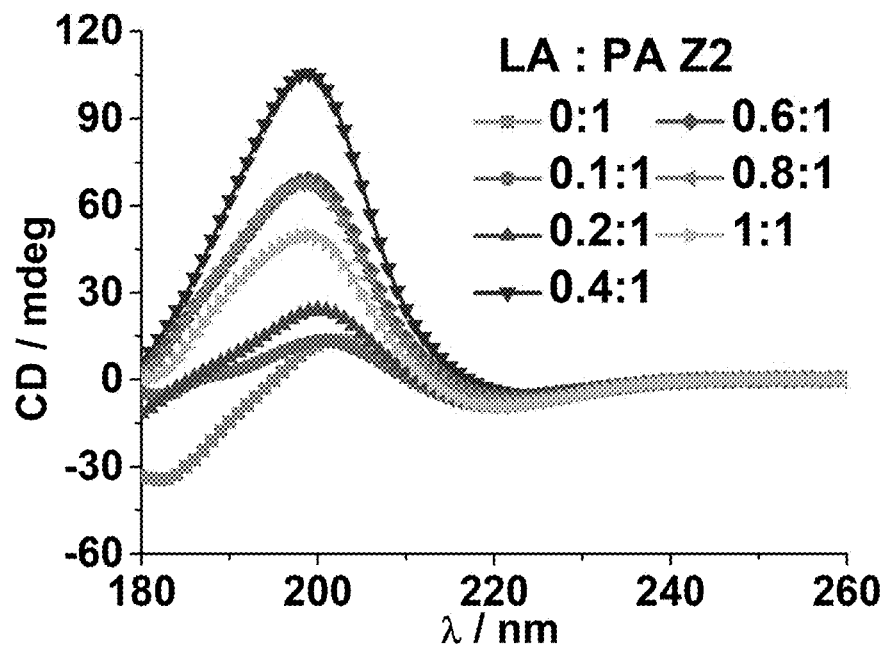
Figure 2C:
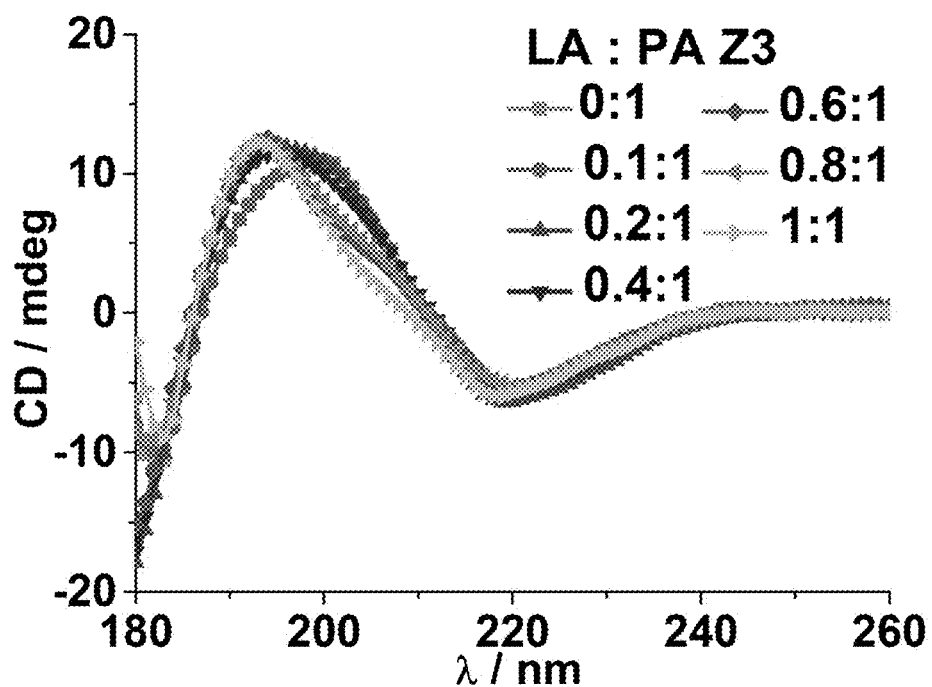
Figure 2D:
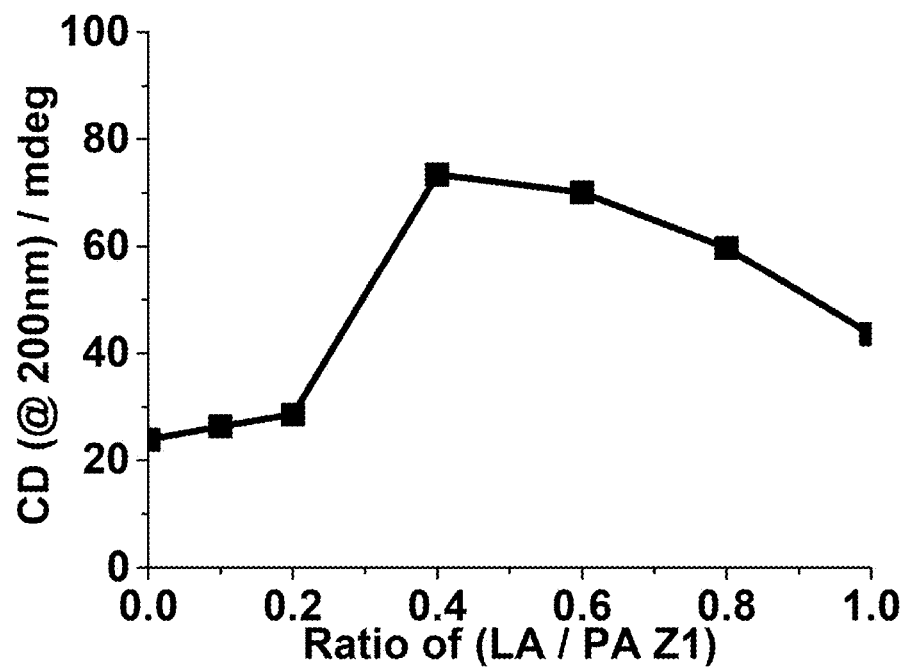
Figure 2E:
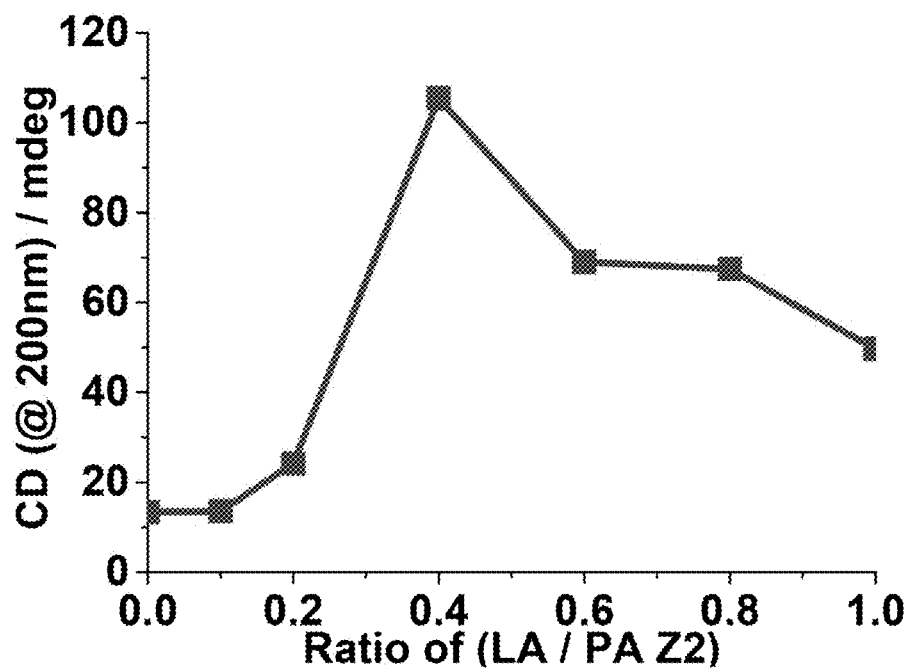
Figure 2F:
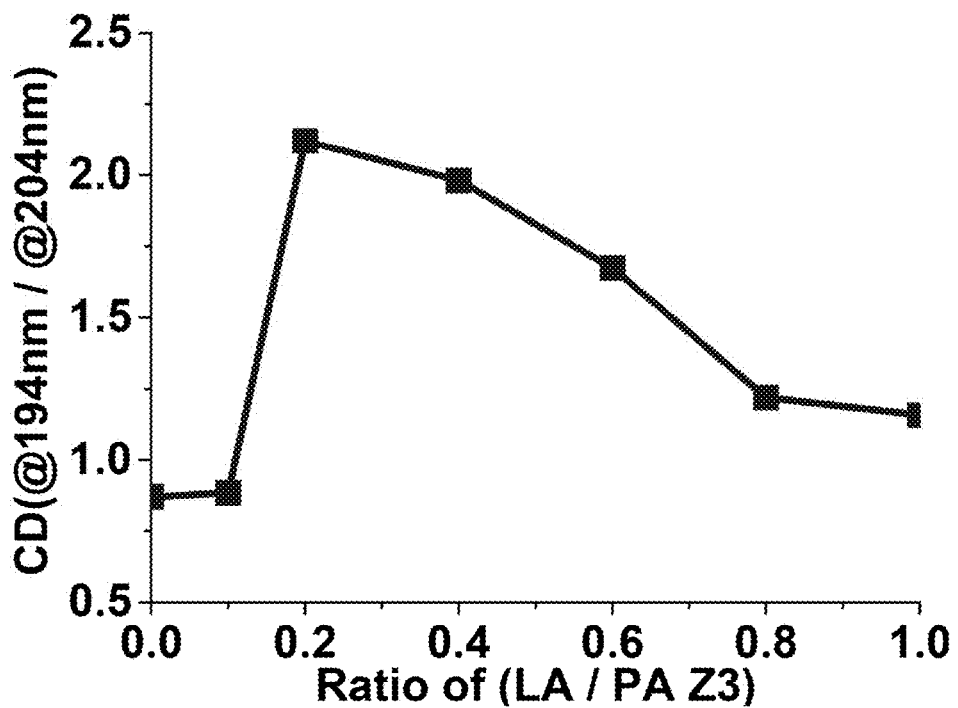
Figure 3A:
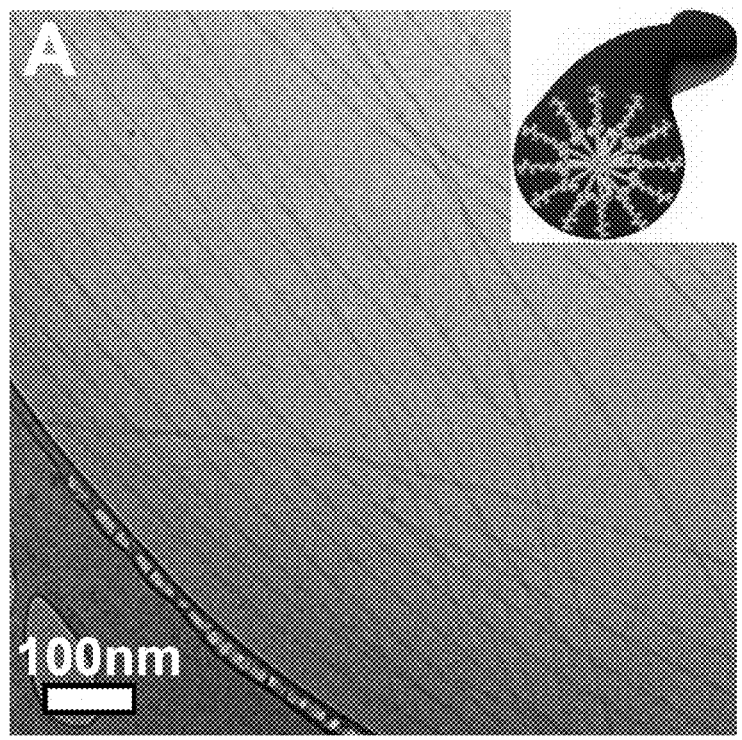
Figure 3B:
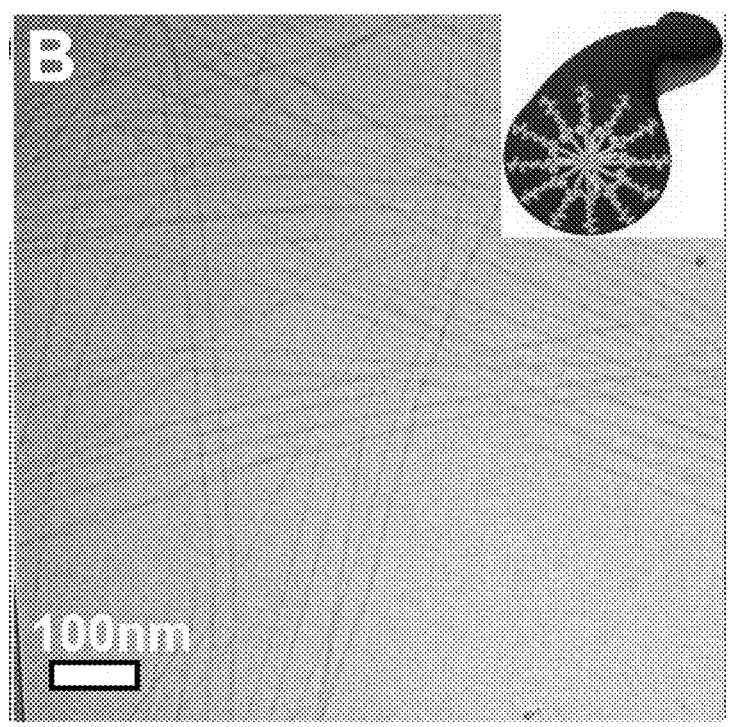

Experiments were conducted during development of embodiments herein to examine the binary co-assembly of designed PAs and lauric acid by CD spectroscopy. Solutions of PA Z1 or Z2 were mixed with lauric acid and then aged for 2 hours at room temperature. The resulting samples showed a substantial increase in CD intensity at 200 nm compared to that of PA solutions alone (FIGS. 2A and 2B), indicating an enhancement of hydrogen bonding among monomers in β-sheets within the assemblies when a small amount of lauric acid is incorporated (refs. 37-38; incorporated by reference in their entireties). The intensity of CD signals at 200 nm reached a maximum value after the addition of approximately 0.4 molar equivalents of lauric acid, and then gradually decreased with further addition (FIGS. 2, D and E). These results indicate that the β-sheet hydrogen bonds are disrupted by associating the PAs Z1 and Z2 with a large fraction of lauric acid. In marked contrast, mixing the solutions of PA Z3 with lauric acid and aging for 2 hours led to a blue shift for the positive Cotton peak across the entire titration process (FIG. 2C). It was conclude that association of PA Z3 assemblies with lauric acid alters the hydrogen bonding of PA monomers in supramolecular assemblies. As a control experiment, the addition of lauric acid to the parent PA without the Z residue yielded an initial increase in the CD intensity up to a value of 0.25 molar equivalents of lauric acid. The invariant CD spectral signature of the parent PA upon addition of greater fractions of lauric acid could be attributed to incomplete encapsulation of additional lauric acid and excess of the lipid likely remains free in solution, potentially due to weak interactions with the parent PA molecules compared with those in binary systems involving PA Z1/Z2/Z3. This result indicates that the incorporation of the Z unit allows the PAs to strongly associate with lauric acid molecules driven by anion-π interactions, thus leading to co-assembly of both components.

To qualitatively verify the anion-α interaction between lauric acid molecules and the PAs, as well as to monitor the location of lauric acid molecules within the assemblies, $^{19}$F NMR experiments were performed on the PAs alone and also on the binary co-assemblies with lauric acid. The ortho-, meta-, and para-fluorine atoms from the phenyl groups were clearly identified in the $^{19}$F NMR spectra. Using the conditions that showed a maximum in the CD intensity, it was found that simultaneously dissolving the PAs and lauric acid in a molar ratio of 1:0.4 led to separation of the signals into two distinct resonances for both the meta- and para-fluorine atoms. In the cases of PA Z1 and PA Z2, the main peaks for the meta- and para-fluorine atoms exhibited down- and upfield shifts, respectively, while the minor peaks of meta- and para-fluorine of PA Z3 displayed down- and upfield shifts, respectively. The substantial separation and shift of the NMR signals of fluorine atoms are in attributable to the anion-π interactions between the PAs and fatty acids (ref. 39; incorporated by reference in its entirety). Although the PAs also contain three carboxylic acids in glutamic acid residues, the fluorine NMR signals on the PAs alone do not show any shift or separation, indicating that anion-π interactions are negligible in PA assemblies. The $^{19}$F NMR results demonstrate that the PAs and lauric acid molecules are successfully co-assembled and associate via anion-π interactions. In particular, positioning the Z residue closer to the N-terminus of the PAs results in greater separation and shift of the fluorine signals, indicating that the PAs interact with lauric acid molecules via anion-π interactions that increase in strength in the following order, PA Z1>PA Z2>PA Z3. The $^{19}$F NMR results also indicate that lauric acid molecules preferentially reside within the hydrophobic core of the PA assemblies. To confirm changes in the $^{19}$F NMR signals induced by anion-π interactions, one trifluoro-ethyl laurate (F-ethyl laurate) without the negatively charged headgroup was used to investigate the effect of its encapsulation on the fluorine signals in the $^{19}$F NMR spectra. In the mixture of F-ethyl laurate and PA Z1, the fluorine signals did not show any shift or separation, indicating that encapsulation of small molecules into the PA assemblies does not give rise to the change of fluorine signals. These additional NMR experiments clearly demonstrate the occurrence of anion-π interactions between the investigated PAs and lauric acid.

The interaction between the PAs and lauric acid was further quantified using isothermal titration calorimetry (ITC; ref. 40; incorporated by reference in its entirety), by recording the thermodynamic parameters obtained upon the addition of lauric acid molecules to pre-formed PA assemblies. The thermodynamic parameters of the formation of the complexes containing PAs and lauric acid in a 1:0.4 molar ratio are shown in Table 1. Addition of lauric acid into all three PA solutions resulted in a negative enthalpy change, indicating the enhancement of β-sheet hydrogen bonds among PA monomers in their assemblies. Only a positive entropy change was observed in the formation of the complex of PA Z1 and lauric acid, indicating the release of structured water molecules (ref. 41; incorporated by reference in its entirety) when these highly favorable interactions occur between PA Z1 and lauric acid carboxylate groups. ITC results confirm that the affinity between lauric acid and the PAs is enhanced due to anion-π interactions, the strength of which varying depending on the location of the Z residue within the PA structure.

TABLE 1

Thermodynamic parameters for the complexes formed between the PA molecules and lauric acid (LA) in a 1:0.4 molar ratio in water at 25° C.

| | PA Z1 + LA | PA Z2 + LA | PA Z3 + LA |
|---|---|---|---|
| Binding Constant/M$^{-1}$ | 5.49 × 10$^4$ ± 5357 | 4.56 × 10$^4$ ± 1215 | 9.95 × 10$^3$ ± 252 |
| ΔH/kcal mol$^{-1}$ | −9.11 ± 0.29 | −2.52 ± 0.24 | −3.64 ± 1.08 |
| ΔS/cal mol$^{-1}$ | 8.86 ± 0.84 | −6.94 ± 0.58 | −12.87 ± 1.34 |
| ΔG/kcal mol$^{-1}$ | −11.75 | −0.45 | 0.19 |

Following the experimental observations of the strong association between the designed PAs and lauric acid molecules, the morphology of the binary co-assemblies was investigated using conventional TEM, cryo-TEM, SAXS. Dissolving in water at the same time PA Z1 or Z2 and lauric acid in a molar ratio of 1:0.4 resulted in the formation of cylindrical nanofibers as revealed by cryo-TEM, similar to the nanostructures formed by the PAs alone. In contrast, mixing PA Z3 with lauric acid in a 1:0.4 molar ratio led to formation of ribbon-like flat nanostructures. This morphological difference between the co-assemblies involving PA Z3 and PA Z1 or Z2 is consistent with the variations of CD spectral changes upon addition of lauric acid, which revealed a blue shift for PA Z3 and an increase in signal intensity for PA Z1 and PA Z2. While intercalation of fatty acids into the hydrophobic interior of the PA cylinders may expand the space between the palmitoyl tails of all three PAs within their corresponding assemblies, the location of the Z residue and fatty acids as well as the strength of noncovalent interactions within the assemblies all contribute to the differences in nanostructures observed with the different PA sequences. In the binary system of PA Z3 and lauric acid, it is contemplated that the co-assembled lipids partially immigrate toward the interior of the β-sheet region driven by anion-t interactions, leading to a small volume ratio of hydrophilic and hydrophobic segments compared with that of supramolecular structures formed by PA Z3 alone. Thus, decrease of the volume ratio gives rise to the morphological transition from cylindrical fibers formed by PA Z3 alone to ribbon-like structures formed by the binary system. However, in the systems consisting of PA Z1 or Z2 and lauric acid, lipids preferentially localize in the hydrophobic core, thus maintaining a relatively large hydrophilic/hydrophobic volume ratio that preserves cylindrical fibers for the binary systems. With further increased the content of lauric acid in the co-assemblies to a 1:1 molar ratio, in contrast to the cylindrical fibers formed by PA Z1 and lauric acid molecules in a 1:0.4 molar ratio, conventional TEM revealed that large vesicles were formed by PA Z1 and lauric acid molecules in a 1:1 molar ratio. Dynamic light scattering confirmed the presence of these large structures and was used to estimate a hydrodynamic radius of approximately 700 nm. On the other hand, mixing PA Z2 or Z3 with lauric acid in a 1:1 molar ratio led to the formation of a heterogeneous collection of cylindrical filaments and vesicles or ribbons and vesicles, respectively, indicating formation of a heterogeneous collection of supramolecular co-assemblies. In the case of PA Z1, the morphological transition for the 1:1 binary co-assemblies is likely the result of a homogeneous geometry change in the complex formed by these two strongly interacting molecules. In contrast, the relatively weak interactions between the other PAs and fatty acids induce formation of binary co-assemblies containing varying amounts of fatty acids, and therefore a heterogeneous mixture of nanostructures.

Figure 4A:
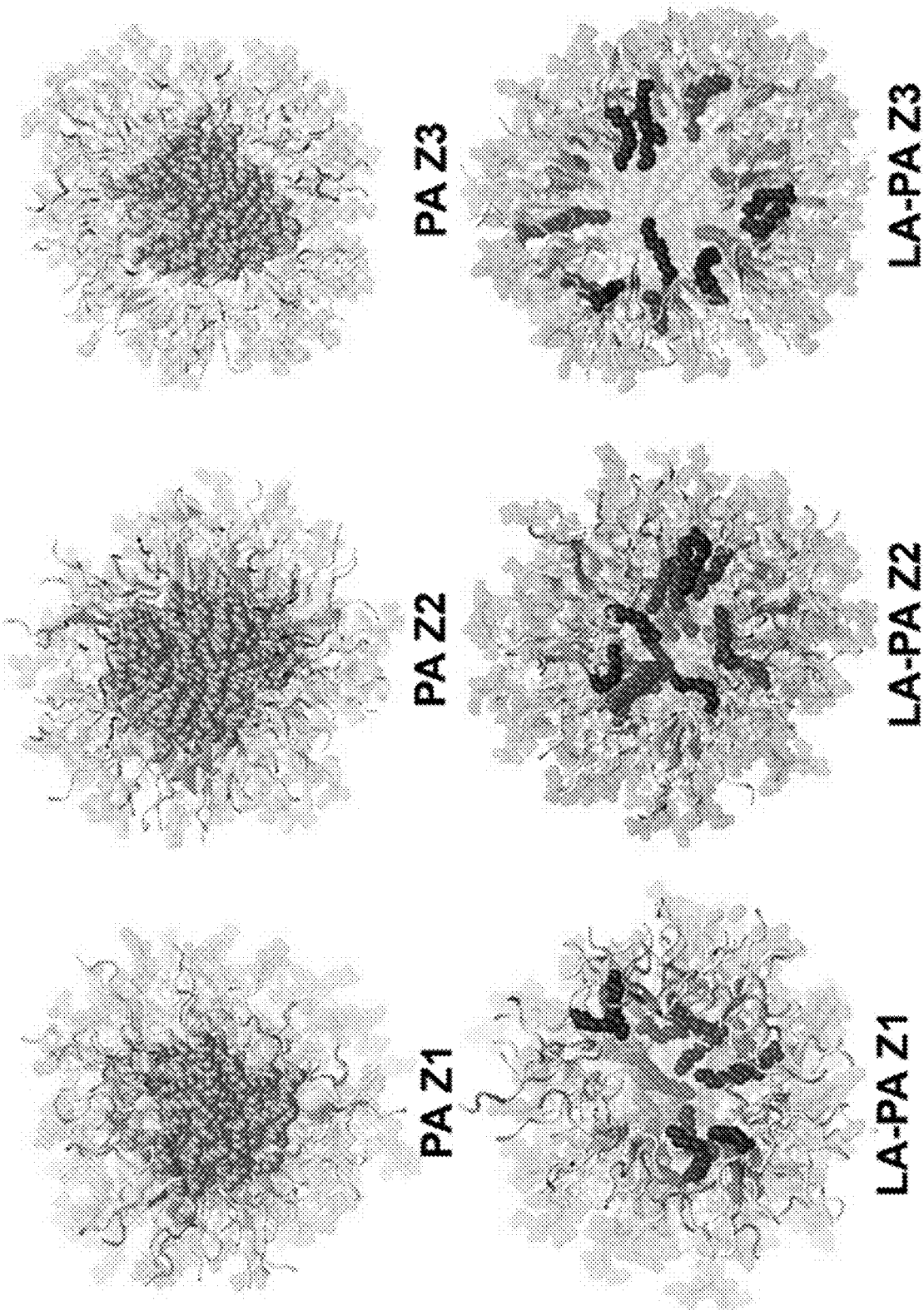
FIGS. 4A-C.
Figure 4B:
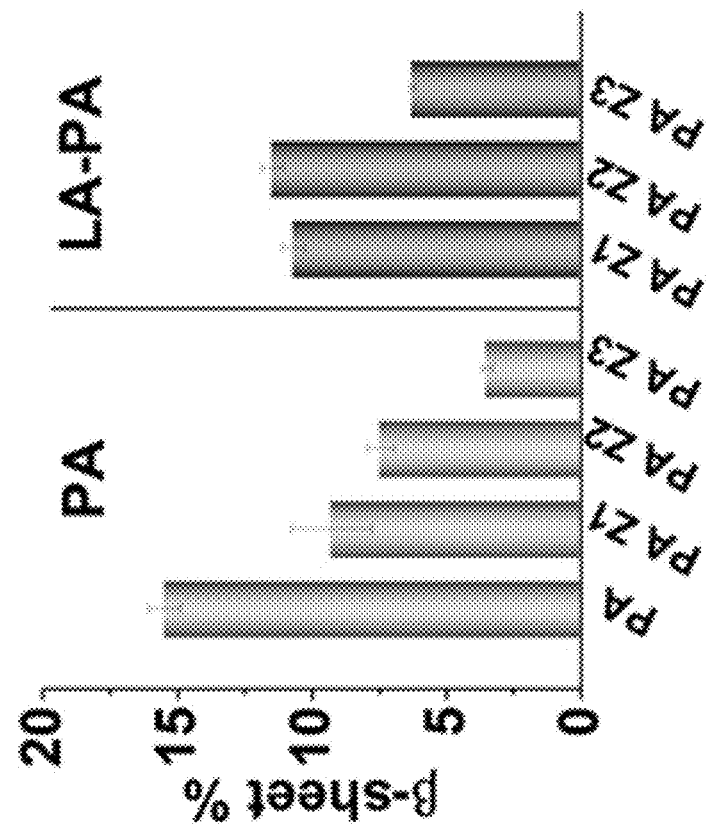

Atomistic molecular dynamics (MD) simulations (ref 42; incorporated by reference in its entirety) were carried out on the co-assemblies of PAs and lauric acid using the Gromacs MD package (ref. 43; incorporated by reference in its entirety) under the GROMOS force field (ref 44; incorporated by reference in its entirety). After 300 ns simulations the secondary structure of peptide segments of PA molecules surrounded by water and sodium counter ions reached a steady state and the cylindrical morphology of the PA assemblies was maintained (FIG. 4A). Compared with the parent PA, the simulation results show that incorporation of the Z residue gives rise to a decrease in β-sheet secondary structure within the assemblies (FIG. 4B). Furthermore, positioning the Z residue closer to the C-terminus (from PA Z1 to Z2 and Z3) gradually lowers the content of β-sheet structures. The simulation results are consistent with experimental findings obtained from the CD intensity of the β-sheets formed by the various PAs. The β-sheet composition was estimated by MD simulations as 9.3%, 7.4%, and 3.5% for PAs Z1, Z2, and Z3, respectively. These results indicate that the bulky Z residue constrains formation of β-sheets potentially due to steric hindrance, which interferes with coupling between hydrogen bond donors and acceptors, particularly when the Z residue is located in the interior of the β-sheet region in the case of PA Z3.

Figure 4C:
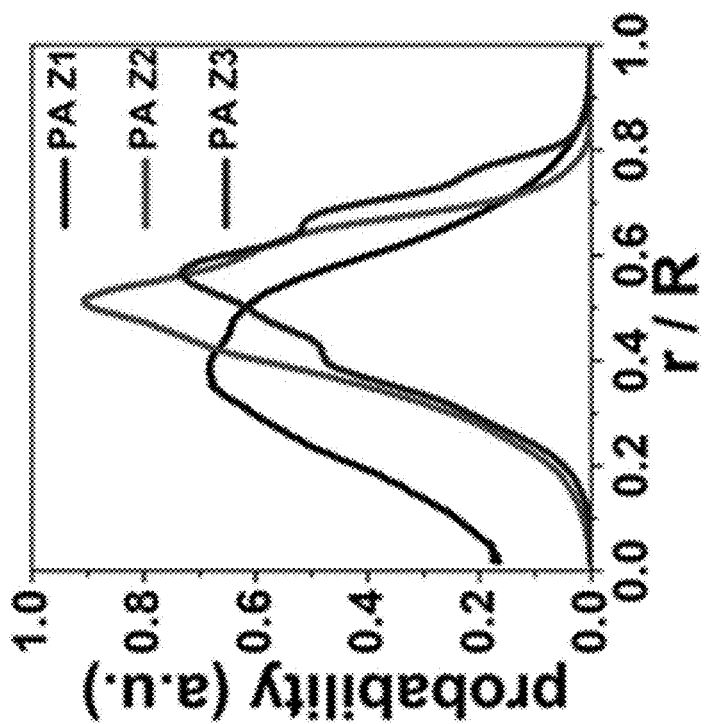

MD simulations on the PA and lauric acid binary systems were carried out under the same condition for the PAs alone. In 300 ns simulation unstable nanofibers were observed in binary co-assemblies of PA Z3 and lauric acid at the 1:0.4 molar ratio, a finding which is consistent with the morphological transitions from cylindrical fibers formed by PA Z3 alone to flat ribbons formed by the binary system in a 1:0.4 molar ratio as observed in TEM experiments. Hence, simulations investigated initial structures consisting of each PA and lauric acid in a 0.2 molar ratio. The lauric acid molecules are localized either randomly or regularly within the initial structures to maximize the reliability of the simulations. After relaxation for at least 200 ns, the initial cylindrical morphology was maintained and the lauric acid molecules reorganized within the fibers (FIG. 4A), indicating that self-assembling the complexes of PAs and LA in a 1:0.2 molar ratio allows for formation of stable, well-defined cylindrical nanofibers. The composition of β-sheets in the complexes increased for all the three PAs as compared with the neat PA assemblies (FIG. 4B). This result is consistent with the experimental observation in CD studies, indicating that encapsulation of lauric acid molecules enables the optimal formation of β-sheet hydrogen bonds within the assemblies. The cross-sectional radial distribution of lauric acid molecules within the stable cylindrical fibers revealed that all of the added lauric acid molecules were confined within the PA assemblies and the radial distribution of lauric acid strongly depends on the position of the Z residue within the PA structures (FIG. 4C). In the case of PA Z1, lauric acid molecules are primarily buried in the hydrophobic core (FIG. 4C, black curve), whereas in the cylindrical fibers formed by PA Z2 or Z3, lauric acid molecules migrate outward relative to the periphery of the fibers. The distribution of the co-assembled lauric acids is associated with the location of the pentafluorobenzene group within the nanofibers (FIG. 4C), indicating that the majority of lauric acid molecules are confined within the area around the Z residue. MD simulations strongly imply that anion-π interactions between the PAs and lauric acid play a critical role in their association, and thus control the location of fatty acids within the co-assemblies.

MD simulations also allow us to further estimate the strength of the π,π-stacking and anion-π interactions within the co-assemblies by evaluating the short-range electrostatic and steric interaction energies per PA monomer. The π,π-stacking interaction energy present in the assemblies formed by PAs alone is nearly identical and determined to be approximately $-25$ kcal mol$^{-1}$ (FIG. 5A), suggesting that the relative distance and orientation of the phenyl groups is independent of their location within the PA structures. However, co-assembling lauric acid with the PAs results in differentiation of the π,π-stacking strength that depends on the position of the Z unit within the peptide backbone. The strength of the π,π-stacking interactions among PA monomers was calculated to be $-15$, $-30$, $-35.3$ kcal mol$^{-1}$ for the binary system containing PA Z1, Z2, and Z3, respectively. These results indicate that the co-assembled lauric acid molecules alter the relative distance and orientation of the aromatic units within the assemblies due to their strong association with the PAs, primarily based on anion-π interactions. The largest increase of the π,π-stacking interactions induced by co-assembly with lauric acid molecules for PA Z3 potentially contributes to the morphological transition from the cylindrical fibers formed by PA Z3 alone to the ribbons formed by the PA-lauric acid complexes, as revealed by the TEM and SAXS experiments discussed above. Generally the simulation results support the concept that supramolecular morphology of the co-assemblies is directly affected by the strength of noncovalent interactions among components.

Based on the atomistic simulations, the anion-π interaction energy between the Z residue and the carboxylic acid unit in lauric acid molecules can increase in the following order: PA Z1>PA Z2>PA Z3 (FIG. 5B). This simulation result confirms that the PA containing the Z unit closer to the N-terminus of peptide backbones exhibits stronger anion-π interactions with lauric acid. This may be attributed to the preferential localization of lauric acid in the hydrophobic core of the co-assemblies, thus leading to a short distance between the electro-deficient aromatic units and carboxylic acids that promotes strong anion-π interactions. Therefore, experiments conducted to profile the radial distribution function (RDF) of the distance between the polar carboxylic acid functional group of lauric acid molecules and the mass center of the pentafluorobenzene rings within the assemblies (FIG. 5C). In the case of PA Z1, the charged head of lauric acid molecules are predominantly localized within 0.4 nm of the aromatic units, a distance which places them in close proximity and favors the anion-7 interaction. However, the primary distance between the carboxylic acid of lauric acid and the mass center of the pentafluorobenzene ring within the PA Z2 and Z3 assemblies increases to 0.6-0.7 nm that is typically associated with lone pair-π interactions (ref 45; incorporated by reference in its entirety), although the distance allowing for anion-π interactions is still observed. This indicates that the main driving force for the association of PA Z2 or Z3 with lauric acid lies in the lone pair-n interactions between the charged head of lauric acid and the fluorinated phenyl groups, accompanied with additional anion-π interactions. Simulation results clearly demonstrate that the anion-π interaction between the PA molecules and lauric acid contributes to their association and determines the location of the encapsulated lauric acid molecules within the co-assemblies.

Example 2

Figure 6:
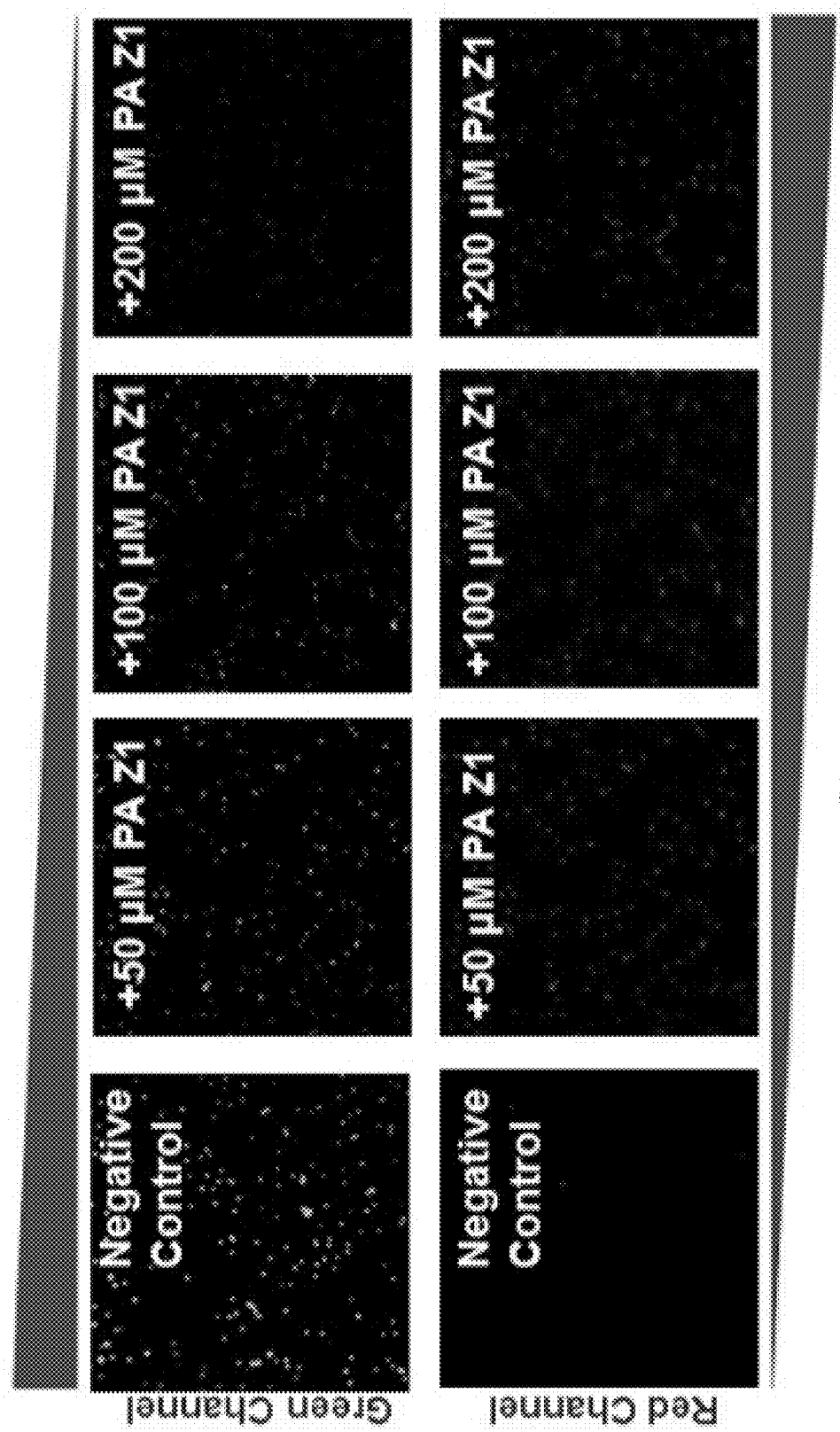
FIG. 6. Visualization of live and dead *S. aureus* cells after treatment with PA Z1 solutions at various concentration. Top: living cells stain positive for intracellular esterase activity reflected in integration with green fluorescent calcein-AM. Bottom: dead cells uptake red fluorescent ethidium homodimer-1 due to loss of plasma membrane integrity. In this assay, Bacteria in PBS (no peptide amphiphiles) served as a negative control.

Experiments were conducted during development of embodiments herein to elucidate the mechanism by which the PA/lipid compositions described herein exert antibacterial activity (FIG. 6); however, embodiments herein are not limited to any particular mechanism of action and an understanding of the mechanism of action is not necessary to practice such embodiments.

Visualization of live and dead *S. aureus* cells after treatment with PA Z1 solutions at various concentration. Top: living cells stain positive for intracellular esterase activity reflected in integration with green fluorescent calcein-AM. Bottom: dead cells uptake red fluorescent ethidium homodimer-1 due to loss of plasma membrane integrity. In this assay, Bacteria in PBS (no peptide amphiphiles) served as a negative control.

Example 3

Figure 7:
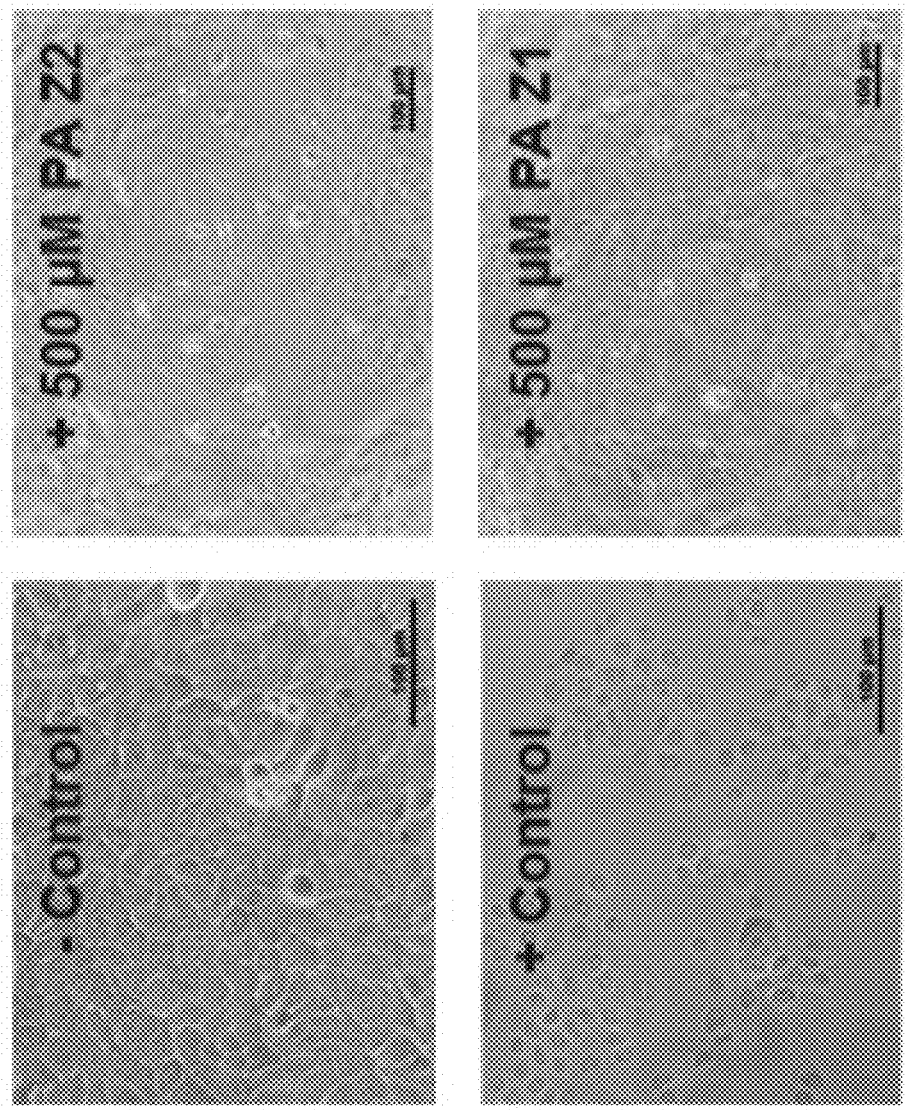
FIG. 7. Brightfield light microscopy of HaCaT (human keratinocytes) cells after treatment with PA Z1 or Z2, where WST-8 is reduced by dehydrogenases in the cells, giving formazan, which was detected with spectrometer at 450 nm. In this assay, while, cells in medium were used as a negative control, Triton X-100 at conc. 1% was used to achieve 100% of cell cytotoxicity as a positive control.

Experiments conducted during development of embodiments herein demonstrate the cytotoxicity of PA/lipid nanostructures against skin cells (FIG. 7). Visualization of HaCaT cells (human keratinocytes) after treatment with PA Z1 or Z2, where WST-8 is reduced by dehydrogenases in the cells, giving formazan, which was detected with spectrometer at 450 nm. In this assay, while, cells in medium were used as a negative control, Triton X-100 at conc. 1% was used to achieve 100% of cell cytotoxicity as a positive control.

Example 4

Critical Aggregation Concentration of Peptide Amphiphiles (PAs)

The critical aggregation concentration (CAC) of PAs Z1, Z2, and Z3 was determined based on encapsulation of a hydrophobic prober 9-diethylamino-5-benzophenoxazinone (Nile Red). The emission of Nile red undergoes blue shift caused upon inclusion in hydrophobic environments. In sample preparation, the concentration of the solutions of PAs Z1, Z2, and Z3 is ranging from 200 nM to 500 μM in PBS buffer, diluting from a stock solution of 2.5 mM. These PA solutions were aged for 1 hour, and Nile Red in ethanol was added to a final concentration of 250 nM. The mixed solutions were aged for another 2 hours before fluorescence experiments. Fluorescence spectroscopy was performed using an ISS PC 1 flourometer in an $_L$-configuration. The solutions were measured in 10 mm quartz cuvette and excited at 550 nm and fluorescence intensity was recorded between 580 and 750 nm. Blue shift of Nile Red emissions were calculated by subtracting the emission wavelength of the sample containing only Nile Red in PBS buffer and were plotted as a function of the concentration of the solutions. The three PAs tested exhibit a CAC of approximately 4 μM.

Figure 11:
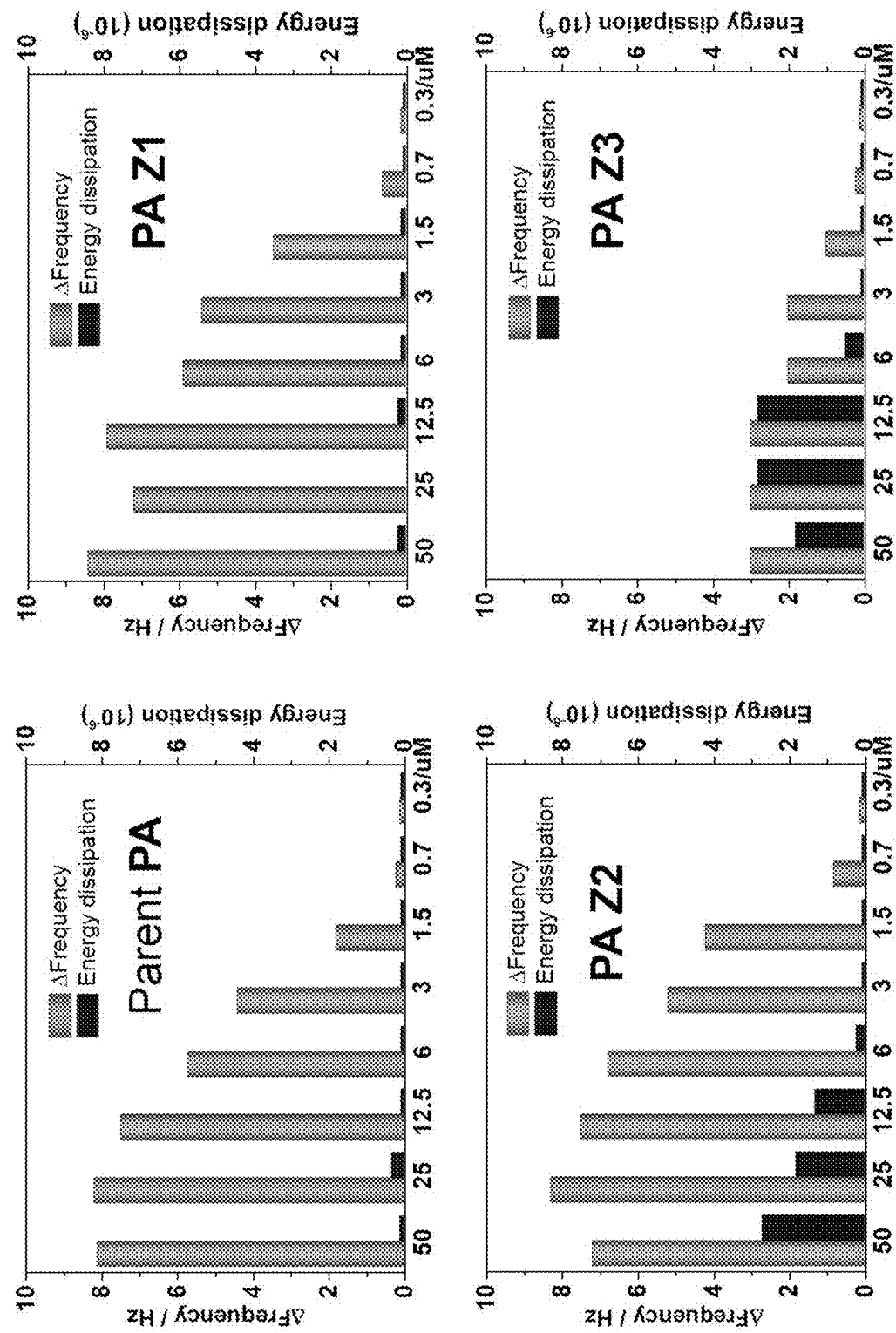
FIG. 11. Shows the absorption of PAs by lipid bilayer. The concentration of the PAs is ranging from 0.3 µM to 500 µM. The PA liquid sample was injected onto the lipid bilayer at a flow rate of 50 µL/min. All four PAs, (parent PA. PAs Z1, Z2, and Z3) were absorbed by the lipid bilayer at a concentration higher than 1.5 M. However, recovery of resonance frequency following the buffer washing step was only observed for parent PA, indicating that the absorption of parent PA is reversible, while the absorption of PAs Z1, Z2, and Z3 is irreversible.

Rheological Experiment (FIG. 11)

The mechanical property of the PAs was evaluated by performing rheological studies. 25 μL of 0.2 M $CaCl_2$ were added to gel 250 μL of 5 mM PA MilliQ-water solution aged for 2 days on the rheometer. Tests were performed at 100 Hz with 0.5% strain at 25° C., using a 25 mm parallel plate with a 0.5 mm gap distance. The storage moduli used were taken from the time test at 5000 seconds. Frequency sweeps were done at a constant strain of 0.5%, and strain sweeps were done at a frequency of 100 Hz. The plateau modulus was determined as 10, 7.5, 7.5, and 2.8 kPa for parent PA, PA Z1, Z2, and Z3, respectively. These results indicate parent PA, PAs Z1, and Z2 form stiff fibers, while the filaments formed by PA Z3 are relatively soft.

Figure 8:
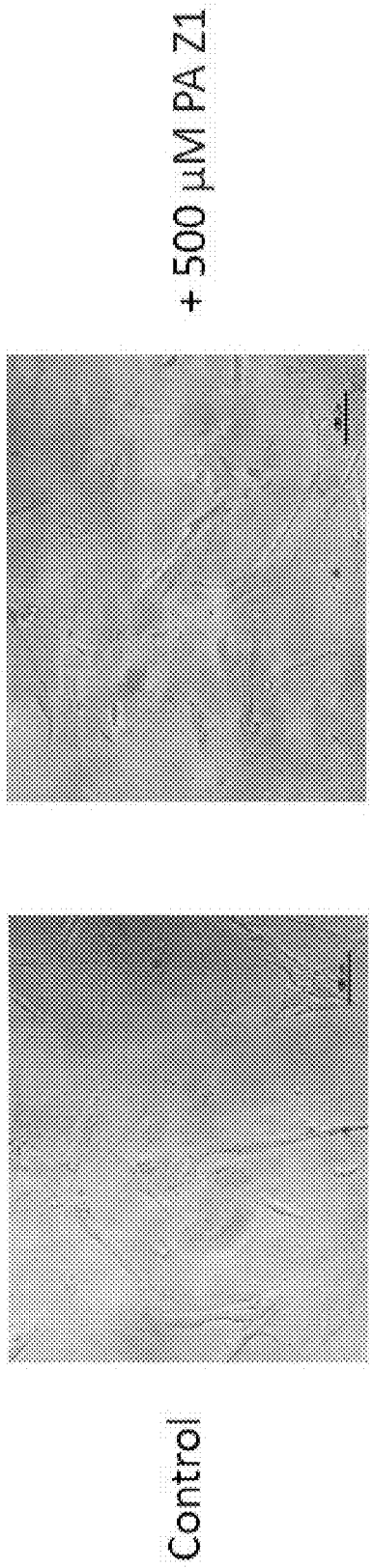
FIG. 8. Shows the biocompatibility of parent PA, PAs Z1, Z2, and Z3 and was assessed by estimating the cytotoxicity of the samples to MRC-5 human fibroblast cell.

Cytotoxicity of PA and PA-LA Complexes (FIG. 8)

The biocompatibility of parent PA, PAs Z1, Z2, and Z3 was assessed by estimating the cytotoxicity of the samples to MRC-5 human fibroblast cell. The concentration of the PA solutions is ranging from 0.3 μM to 500 μM, and the MRC-5 human fibroblast cell number was $5 \times 10^3$. CCK-8 assay was performed in order to measure dehydrogenase activity. Eventually, up to the concentration of 500 μM, no obvious or less than 20% drop of cell viability was observed after treatment of the cells by PA solutions, and this result is quite comparable to the cells treated with PBS buffer. Results indicate that the PAs exhibit great biocompatibility to healthy human cells.

Recorded Minimum Inhibitory Concentrations (FIG. 9)

The minimum inhibitory concentration (MIC) of the PAs against Staphylococcus aureus was determined to estimate their bioactivity as antimicrobial agents. The bacterial cell density is $5 \times 10^5$ CFU/mL, and the concentration of the PA solutions is ranging from 0.3 μM to 500 μM. By optical density measurements on cell suspensions, the MIC value for PAs Z1 and Z2 was determined to be 4 μM, while inhibition of the growth of the bacterium after treatment by parent PA and PA Z3 at 500 μM was not observed. This result indicate that PAs Z1 and Z2 possess great bioactivity to inhibit the bacterial growth compared to parent PA and PA Z3.

Figure 10:
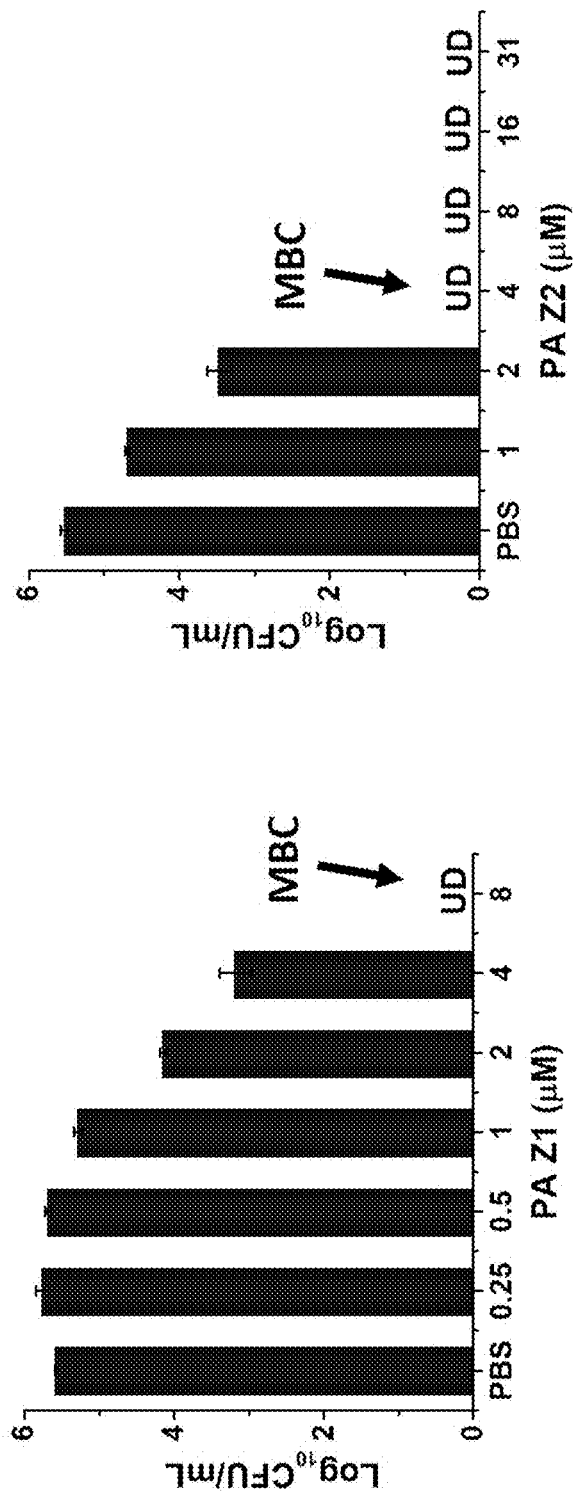
FIG. 10. Shows the minimum bactericidal concentration (MBC) of PAs Z1 and Z2 against Staphylococcus aureus.

Recorded Minimum Bactericidal Concentration (FIG. 10)

The minimum bactericidal concentration (MBC) of PAs Z1 and Z2 against Staphylococcus aureus was determined to decipher whether the PAs are bactericidal or bacteriostatic agents. The bacterial cell density is $5 \times 10^5$ CFU/mL, and the concentration of the PA solutions is ranging from 0.3 μM to 500 μM. It was found that treatment of Staphylococcus aureus by PAs Z1 and Z2 at a concentration of 8 μM and 4 μM resulted in complete bacterial death, indicative of a bactericidal agent for PAs Z1 and Z2.

Absorption of PAs by Artificial Lipid Bilayer (FIG. 11)

To gain insight into the mechanism of the bioactivity of the PAs, the absorption of the PAs by artificial lipid bilayer was investigated. The artificial lipid bilayer was prepared using a 1,2-dioleoylsn glycero-3-phosphocholine (DOPC) lipid based on solvent-assisted lipid bilayer technique. A 0.5 mg/mL solution of DOPC in isopropanol was added to silicon substrate and allowed to equilibrate for 10 min followed by exchange with PBS buffer to form the supported lipid bilayer. Subsequently 50 μM bovine serum albumin was added as a blocking agent to prevent the nonspecific adsorption of antibacterial agents in experiments. After the bilayer formation, the solution was exchanged with PBS solution, and then the test compound in an identical PBS solution was added under continuous flow conditions for a minimum of 30 min. A washing step with PBS solution was conducted to complete the process. The concentration of the PAs is ranging from 0.3 LM to 500 μM. The PA liquid sample was injected onto the lipid bilayer at a flow rate of 50 μL/min. All four PAs, (parent PA, PAs Z1, Z2, and Z3) were absorbed by the lipid bilayer at a concentration higher than 1.5 μM. However, recovery of resonance frequency following the buffer washing step was only observed for parent PA, indicating that the absorption of parent PA is reversible, while the absorption of PAs Z1, Z2, and Z3 is irreversible.

Figure 12:
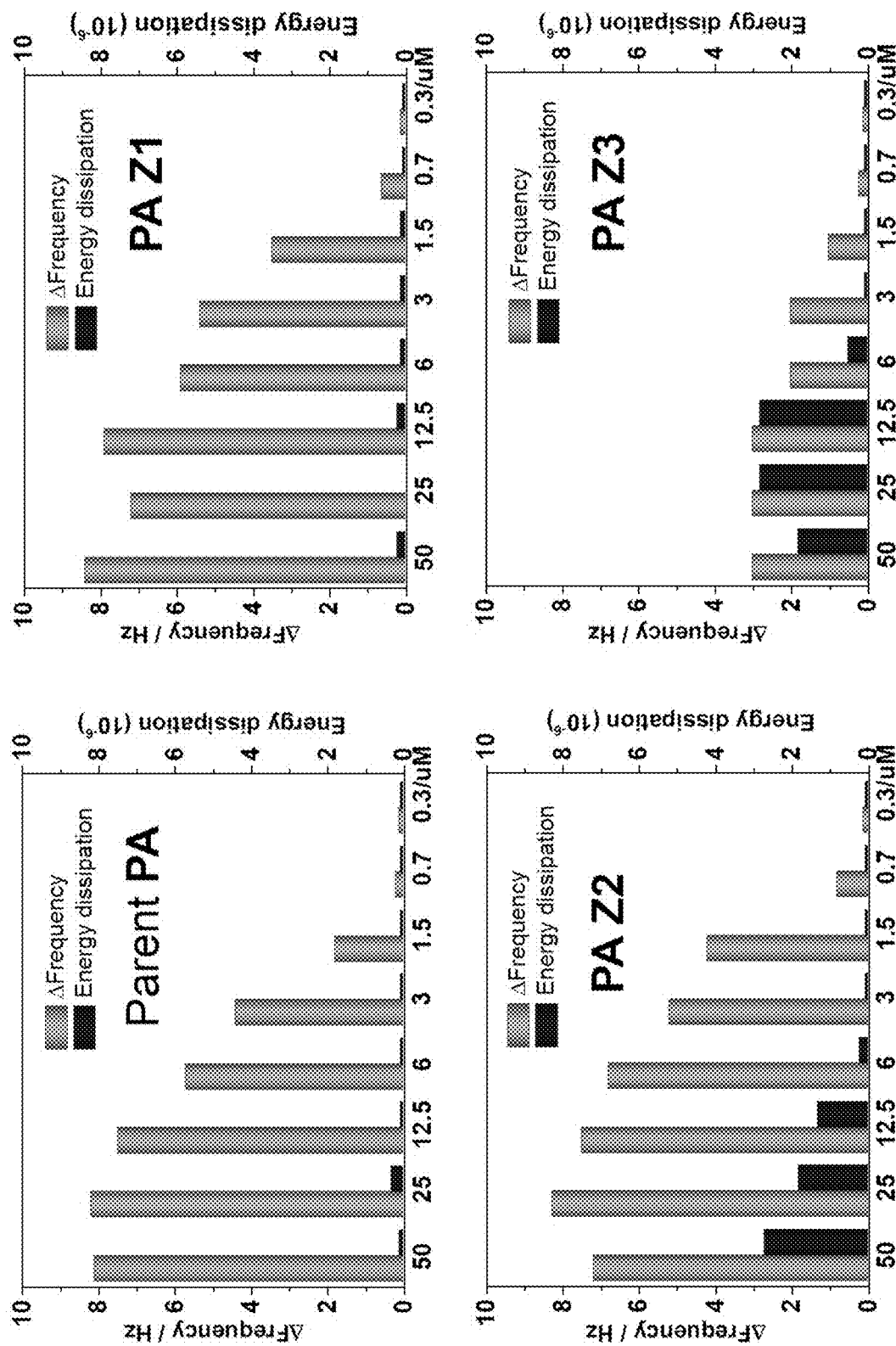
FIG. 12. Shows the absorption of PAs by lipid bilayer. It was determined that the absorbed amount of parent PA, PAs Z1, and Z2 as a function of the concentration of the solutions is more or less identical, while is larger than that of PA Z3, reminiscent of an efficient uptake of parent PA. PAs Z2, and Z2 and a poor absorption for PA Z3.

Absorption of PAs by Artificial Lipid Bilayer (FIG. 12)

The absorbed amount of the PAs depends on the structure of the PAs and the concentration of the solutions. It was determined that the absorbed amount of parent PA, PAs Z1, and Z2 as a function of the concentration of the solutions is more or less identical, while is larger than that of PA Z3, reminiscent of an efficient uptake of parent PA, PAs Z2, and Z2 and a poor absorption for PA Z3. These results indicate that only stiff fibers, such as those formed by parent PA, PAs Z1, and Z2, are efficiently absorbed by the lipid bilayer. Absorption of PAs Z2 and Z3 caused a large energy dissipation compared to parent PA and PA Z1. In the case of PA Z2, the large energy dissipation mostly results from the change of the structural order of the lipid bilayer arising from the absorption of PA Z2. However the large energy dissipation change observed in the experiments involving PA Z3 is attributable to the low stiffness of the absorbed PA fibers as determined by the rheological experiments.

Figure 13:
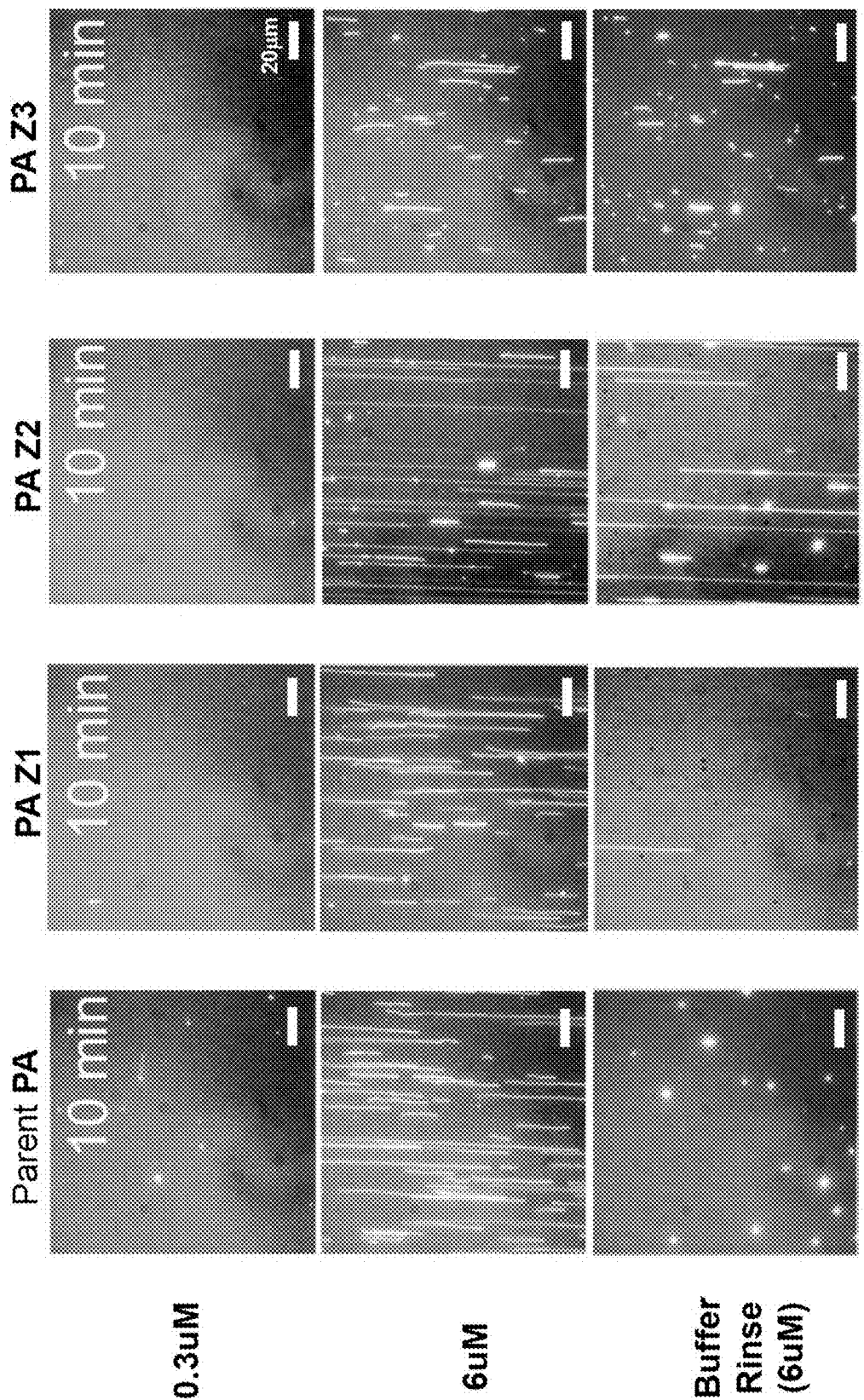
FIG. 13. Shows the results of fluorescence microscopy performed to directly observe morphological changes in supported lipid bilayers upon treatment with the PAs.

Fluorescence Microscopy Experiments (FIG. 13)

Fluorescence microscopy was performed to directly observe morphological changes in supported lipid bilayers upon treatment with the PAs. The pixel size was 0.267× 0.267 µm$^2$. A fiber-coupled mercury lamp (Intensilight C-HGFIE, Nikon) was used to illuminate the fluorophores with a TRITC filter. The composition of the supported lipid bilayer was 99.5 mol % DOPC lipid and 0.5 mol % 1,2-dipalmitoyl-sn-glycero-3-phosphoethanolamine-N-(lissamine rhodamine B sulfonyl) lipid. The lipid bilayer was formed by the vesicle fusion method (0.2 mg/mL extruded DOPC lipid vesicles with 68 nm diameter) inside a microfluidic flow-through chamber. After formation, the lipid bilayer was rinsed with buffer solution, and then the test compound was introduced into the measurement chamber at a flow rate of 40 µL/min. During this stage, time-lapse images were recorded every 5 s for a total duration of 30 min. The initial time, t=0 s, was defined by when the test compound solution reached the channel inlets. For each measurement recorded, the fluorescence intensity of each image was normalized using a custom-written script for the Python(x,y) 2.7.5 software program. It was found that absorption of the PAs by the lipid bilayer leads to formation of tubular protrusions. The area covered by tubular protrusions induced by absorption of parent PA, PAs Z1, and Z2 is more or less identical, but larger than that of PA Z3. This observation is consistent with the absorption amount of the PAs as determined by QCM-D studies. Rinsing the lipid bilayer in which the PAs are absorbed with buffer solution results in different structural features. In the case of parent PA and PA Z3, the lipid bilayer is more or less intact, although some white spots were observed. However, washing PAs Z2 and Z3 from the lipid bilayer led to formation of many dark pores. These results indicate that the PAs Z2 and Z3 insert into the deep region of the lipid bilayer, while parent PA and PA Z3 are only absorbed in the shallow area of the lipid bilayer. The low absorption amount of PA Z3 also prevents the change of the structure of the lipid bilayer. The localization of PAs Z2 and Z3 in the deep region of the lipid bilayer might be attributed to their strong association with lipid due to the anion-π interactions between the electron-deficient aromatic group and the carboxylic groups of the lipids. Although parent PA was absorbed efficiently by the lipid bilayer, the weak affinity to the lipids only allows them to be absorbed on the surface or the shallow area of the lipid bilayer.

Combining QCM-D studies with fluorescence experiments, it was concluded that the PAs that form stiff cylindrical fibers could be efficiently absorbed by the lipid bilayer. The PAs with strong association with lipids could insert into the lipid bilayer deeply, resulting in the changes of the lipid bilayer structures. This summary of the absorption of the PAs by artificial lipid bilayer potentially could be applied to the interaction between the PAs and cell membrane or cell wall of bacteria. The efficient absorption of PAs Z1 and Z2 and the resulting changes of cell membrane or cell wall contribute to the remarkable bioactivity to inhibit bacterial growth and kill bacteria as antimicrobial agents.

REFERENCES

The following references, some of which are cited above by number, are herein incorporated by reference in their entireties.

(1) Webber, M. J.; Appel, E. A.; Meijer, E. W.; Langer, R. Supramolecular biomaterials. Nat Mater 2016, 15, 13-26.

(2) Silva, G. A.; Czeisler, C.; Niece, K. L.; Beniash, E.; Harrington, D. A.; Kessler, J. A.; Stupp, S. I. Science 2004, 303, 1352.

(3) Dankers, P. Y. W.; Harmsen, M. C.; Brouwer, L. A.; Van Luyn, M. J. A.; Meijer, E. W. A modular and supramolecular approach to bioactive scaffolds for tissue engineering. Nat Mater 2005, 4, 568-574.

(4) Soukasene. S.; Toft, D. J.; Moyer, T. J.; Lu, H.; Lee, H.-K.; Standley, S. M.; Cryns, V. L.; Stupp, S. I. Antitumor Activity of Peptide Amphiphile Nanofiber-Encapsulated Camptothecin. ACS Nano 2011, 5, 9113-9121.

(5) Anraku, Y.; Kishimura, A.; Kamiya, M.; Tanaka, S.; Nomoto, T.; Toh, K.; Matsumoto, Y.; Fukushima, S.; Sueyoshi, D.; Kano, M. R.; Urano, Y.; Nishiyama, N.; Kataoka, K. Systemically Injectable Enzyme-Loaded Polyion Complex Vesicles as In Vivo Nanoreactors Functioning in Tumors. Angew. Chem. Int. Ed. 2016, 55, 560-565.

(6) Ringler, P.; Schulz, G. E. Self-Assembly of Proteins into Designed Networks. Science 2003, 302, 106-109.

(7) Davis, M. E.; Zuckerman, J. E.; Choi, C. H. J.; Seligson, D.; Tolcher, A.; Alabi, C. A.; Yen, Y.; Heidel, J. D.; Ribas, A. Evidence of RNAi in humans from systemically administered siRNA via targeted nanoparticles. Nature 2010, 464, 1067-1070.

(8) Gu, F.; Zhang, L.; Teply, B. A.; Mann, N.; Wang, A.; Radovic-Moreno, A. F.; Langer, R.; Farokhzad, O. C. Precise engineering of targeted nanoparticles by using self-assembled biointegrated block copolymers. Proc. Natl. Acad. Sci. U.S.A 2008, 105, 2586-2591.

(9) Discher, D. E.; Eisenberg, A. Polymer Vesicles. Science 2002, 297, 967-973.

(10) Percec. V.; Wilson, D. A.; Leowanawat, P.; Wilson, C. J.; Hughes, A. D.; Kaucher, M. S.; Hammer, D. A.; Levine, D. H.; Kim, A. J.; Bates, F. S.; Davis, K. P.; Lodge, T. P.; Klein. M. L.; DeVane, R. H.; Aqad, E.; Rosen, B. M.; Argintaru. A. O.; Sienkowska, M. J.; Rissanen, K; Nummelin, S.; Ropponen, J. Self-Assembly of Janus Dendrimers into Uniform Dendrimersomes and Other Complex Architectures. Science 2010, 328, 1009-1014.

(11) Huang, Y.; Chiang, C.-Y.; Lee, S. K.; Gao, Y.; Hu. E. L.; Yoreo, J. D.; Belcher, A. M. Programmable Assembly of Nanoarchitectures Using Genetically Engineered Viruses. Nano Lett. 2005, 5, 1429-1434.

(12) Hobza, P.; Řezáč, J. Introduction: Noncovalent Interactions. Chem. Rev. 2016, 116, 4911-4912.

(13) Cui, H.; Webber, M. J.; Stupp, S. I. Self-assembly of peptide amphiphiles: From molecules to nanostructures to biomaterials. Peptide Science 2010, 94, 1-18.

(14) Cook, T. R.; Stang, P. J. Recent Developments in the Preparation and Chemistry of Metallacycles and Metallacages via Coordination. Chem. Rev. 2015, 115, 7001-7045.

(15) Würthner, F.; Saha-Möller, C. R.; Fimmel, B.; Ogi, S.; Leowanawat, P.; Schmidt, D. Perylene Bisimide Dye Assemblies as Archetype Functional Supramolecular Materials. Chem. Rev. 2016, 116, 962-1052.

(16) Meyer, E. A.; Castellano, R K.; Diederich, F. Interactions with Aromatic Rings in Chemical and Biological Recognition. Angew. Chem. Int. Ed. 2003, 42, 1210-1250.

(17) Ma. J. C.; Dougherty, D. A. The Cation-π Interaction. Chem. Rev. 1997, 97, 1303-1324.

(18) Quiñonero, D.; Garau, C.; Rotger, C.; Frontera. A.; Ballester, P.; Costa, A.; Deyà, P. M. Anion-n Interactions: Do They Exist? Angew. Chem. Int. Ed. 2002, 41, 3389-3392.

(19) Schottel, B. L.; Chifotides, H. T.; Dunbar, K R. Anion-pi interactions. Chem. Soc. Rev. 2008, 37, 68-83.

(20) Frontera, A.; Gamez, P.; Mascal, M.; Mooibroek, T. J.; Reedijk, J. Putting anion-pi interactions into perspective. Angew. Chem. Int. Ed. 2011, 50, 9564-9583.

(21) de Hoog, P.; Gamez, P.; Mutikainen, I.; Turpeinen, U.; Reedijk, J. An aromatic anion receptor: anion-pi interactions do exist. Angew. Chem. Int. Ed. 2004, 43, 5815-5817.

(22) Dawson, R. E.; Hennig, A.; Weimann, D. P.; Emery. D.; Ravikumar, V.; Montenegro, J.; Takeuchi, T.; Gabutti, S.; Mayor, M.; Mareda. J.; Schalley, C. A.; Matile, S. Experimental evidence for the functional relevance of anion-pi interactions. Nat. Chem. 2010, 2, 533-538.

(23) Perraud, O.; Robert, V.; Gornitzka, H.; Martinez, A.; Dutasta, J. P. Combined cation-pi and anion-pi interactions for zwitterion recognition. Angew. Chem. Int. Ed. 2012, 51, 504-508.

(24) Zhao, Y.; Cotelle, Y.; Sakai. N.; Matile, S. Unorthodox Interactions at Work. J. Am. Chem. Soc. 2016, 138, 4270-4277.

(25) Giese, M.; Albrecht, M.; Rissanen, K. Experimental investigation of anion-[small pi] interactions—applications and biochemical relevance. Chem. Commun. 2016, 52, 1778-1795.

(26) Cotelle, Y.; Lebrun, V.; Sakai, N.; Ward, T. R.; Matile, S. Anion-π Enzymes. ACS Central Science 2016, 2, 388-393.

(27) Lucas, X; Bauza, A.; Frontera, A.; Quinonero, D. A thorough anion-[small pi]interaction study in biomolecules: on the importance of cooperativity effects. Chemical Science 2016, 7, 1038-1050.

(28) Hartgerink, J. D.; Beniash, E.; Stupp, S. I. Self-Assembly and Mineralization of Peptide-Amphiphile Nanofibers. Science 2001, 294, 1684-1688.

(29) Pashuck, E. T.; Stupp, S. I. Direct Observation of Morphological Transformation from Twisted Ribbons into Helical Ribbons. J. Am. Chem. Soc. 2010, 132, 8819-8821.

(30) Moyer, T. J.; Cui. H.; Stupp, S. I. Tuning Nanostructure Dimensions with Supramolecular Twisting. J. Phys. Chem. B 2013, 117, 4604-4610.

(31) Cui, H.; Cheetham, A. G.; Pashuck, E. T.; Stupp, S. I. Amino Acid Sequence in Constitutionally Isomeric Tetrapeptide Amphiphiles Dictates Architecture of One-Dimensional Nanostructures. J. Am. Chem. Soc. 2014, 136, 12461-12468.

(32) Douliez, J.-P.; Gaillard, C. Self-assembly of fatty acids: from foams to protocell vesicles. New Journal of Chemistry 2014, 38, 5142-5148.

(33) Fameau, A.-L.; Zemb, T. Self-assembly of fatty acids in the presence of amines and cationic components. Advances in Colloid and Interface Science 2014, 207, 43-64.

(34) Jackman, J.; Yoon, B.; Li, D.; Cho, N.-J. Nanotechnology Formulations for Antibacterial Free Fatty Acids and Monoglycerides. Molecules 2016, 21, 305.

(35) Pace, C. J.; Gao, J. Exploring and exploiting polar-pi interactions with fluorinated aromatic amino acids. Acc. Chem. Res. 2013, 46, 907-915.

(36) Pashuck, E. T.; Cui, H.; Stupp, S. I. Tuning Supramolecular Rigidity of Peptide Fibers through Molecular Structure. J. Am. Chem. Soc. 2010, 132, 6041-6046.

(37) Hong, D.-P.; Hoshino, M.; Kuboi, R.; Goto, Y. Clustering of Fluorine-Substituted Alcohols as a Factor Responsible for Their Marked Effects on Proteins and Peptides. J. Am. Chem. Soc. 1999, 121, 8427-8433.

(38) Gursky, O.; Aleshkov, S. Temperature-dependent β-sheet formation in β-amyloid Aβ1-40 peptide in water: uncoupling β-structure folding from aggregation. Biochimica et Biophysica Acta (BBA)—Protein Structure and Molecular Enzymology 2000, 1476, 93-102.

(39) Giese, M.; Albrecht. M.; Repenko, T.; Sackmann, J.; Valkonen, A.; Rissanen, K. Single-Crystal X-ray Diffraction and Solution Studies of Anion-π Interactions in N-(Pentafluorobenzyl)pyridinium Salts. Eur. J. Org. Chem. 2014, 2014, 2435-2442.

(40) Tsamaloukas, A. D.; Keller, S.; Heerklotz, H. Uptake and release protocol for assessing membrane binding and permeation by way of isothermal titration calorimetry. Nat. Protocols 2007, 2, 695-704.

(41) Rekharsky, M. V.; Mori, T.; Yang, C.; Ko, Y. H.; Selvapalam, N.; Kim, H.; Sobransingh, D.; Kaifer, A. E.; Liu. S.; Isaacs, L.; Chen, W.; Moghaddam, S.; Gilson, M. K.; Kim, K.; Inoue, Y. A synthetic host-guest system achieves avidin-biotin affinity by overcoming enthalpy-entropy compensation. Proc. Natl. Acad. Sci. U.S.A 2007, 104, 20737-20742.

(42) Lee, O.-S.; Stupp, S. I.; Schatz, G. C. Atomistic Molecular Dynamics Simulations of Peptide Amphiphile Self-Assembly into Cylindrical Nanofibers. J. Am. Chem. Soc. 2011, 133, 3677-3683.

(43) Berendsen, H. J. C.; Postma, J. P. M.; van Gunsteren, W. F.; Hermans, J.; Interaction Models for Water in Relation to Protein Hydration. In Intermolecular Forces: Proceedings of the Fourteenth Jerusalem Symposium on Quantum Chemistry and Biochemistry Held in Jerusalem, Israel, Apr. 13-16, 1981; Pullman, B., Ed.; Springer Netherlands: Dordrecht, 1981: pp 331-342.

(44) Scott. W. R. P.; Hunenberger, P. H.; Tironi, I. G.; Mark, A. E.; Billeter, S. R; Fennen, J.; Torda, A. E.; Huber, T.; Kruger, P.; van Gunsteren, W. F. The GROMOS biomolecular simulation program package. J Phys Chem A 1999, 103, 3596-3607.

(45) Jain, A.; Ramanathan, V.; Sankararamakrishnan, R. Lone pair •~• π interactions between water oxygens and aromatic residues: Quantum chemical studies based on high-resolution protein structures and model compounds. Protein Science 2009, 18, 595-605.

The invention claimed is:

1. A peptide amphiphile comprising a non-peptide hydrophobic tail, a structural peptide segment, and a charged peptide segment, wherein one amino acid in the peptide amphiphile is a pentafluorophenylalanine (Z) residue, wherein the hydrophobic tail is linked to the N-terminus of the structural peptide segment, and the C-terminus of the structural peptide segment is linked to the N-terminus of the charged peptide segment, wherein (1) the structural peptide segment comprises ZVVAAA (SEQ ID NO: 1), VZVAAA (SEQ ID NO: 2), VVZAAA (SEQ ID NO: 3), VVVZAA (SEQ ID NO: 4), VVVAZA (SEQ ID NO: 5), or VVVAAZ (SEQ IS NO: 6), (2) the charged peptide segment comprises ZE (SEQ ID NO: 29), EZ (SEQ ID NO: 30), ZEE (SEQ ID NO: 31), EZE (SEQ ID NO: 32), or EEZ (SEQ ID NO: 33), or (3) both (1) and (2).

2. The peptide amphiphile of claim 1, wherein the non-peptide hydrophobic tail comprises an acyl chain of 6 to 24 carbons in length.

3. The peptide amphiphile of claim 1, wherein the structural peptide segment and the charged peptide segment comprise ZVVAAAEEE (SEQ ID NO: 9), VZVAAAEEE (SEQ ID NO: 10), VVZAAAEEE (SEQ ID NO: 11), VVVZAAEEE (SEQ ID NO: 12), VVVAZAEEE (SEQ ID NO: 13), VVVAAZEEE (SEQ ID NO: 14), VVVAAAZEE (SEQ ID NO: 15), VVVAAAEZE (SEQ ID NO: 16), or VVVAAAEEZ (SEQ ID NO: 17).

4. A nanofiber comprising the peptide amphiphile of claim 1.

5. A supramolecular structure comprising a peptide amphiphile of claim 1 and a lipid molecule.

6. The supramolecular structure of claim 5, wherein the lipid molecule is a fatty acid.

7. The supramolecular structure of claim 5, wherein the fatty acid and the non-peptide hydrophobic tail have an equal number of carbon atoms.

8. A method of treating a bacterial infection comprising administering a supramolecular structure of claim 5 to a subject in need thereof.

9. The method of claim 8, wherein the bacteria is antibiotic resistant.

10. The method of claim 8 wherein the supramolecular structure is administered with an antibiotic agent.

* * * * *

UNITED STATES PATENT AND TRADEMARK OFFICE
CERTIFICATE OF CORRECTION

| | |
|---|---|
| PATENT NO. | : 10,752,656 B2 |
| APPLICATION NO. | : 15/789279 |
| DATED | : August 25, 2020 |
| INVENTOR(S) | : Samuel I. Stupp et al. |

It is certified that error appears in the above-identified patent and that said Letters Patent is hereby corrected as shown below:

In the Specification

In Column 1, Line 14, please correct the government funding statement to read:
-- This invention was made with government support under grant number DMR1508731 awarded by the National Science Foundation. The government has certain rights in the invention. --

Signed and Sealed this
Twenty-eighth Day of November, 2023

Katherine Kelly Vidal
*Director of the United States Patent and Trademark Office*